(12) United States Patent
Trabolsi et al.

(10) Patent No.: US 9,849,194 B2
(45) Date of Patent: Dec. 26, 2017

(54) COMPOSITIONS AND METHODS FOR IMAGING AND TREATMENT

(71) Applicant: New York University, New York, NY (US)

(72) Inventors: Ali Trabolsi, Abu Dhabi (AE); Farah Benyettou, Abu Dhabi (AE)

(73) Assignee: New York University, New York, NY (US)

(*) Notice: Subject to any disclaimer, the term of this patent is extended or adjusted under 35 U.S.C. 154(b) by 198 days.

(21) Appl. No.: 14/818,544

(22) Filed: Aug. 5, 2015

(65) Prior Publication Data

US 2016/0038610 A1  Feb. 11, 2016

Related U.S. Application Data

(60) Provisional application No. 62/033,249, filed on Aug. 5, 2014.

(51) Int. Cl.
| | |
|---|---|
| *A61K 47/48* | (2006.01) |
| *A61K 31/337* | (2006.01) |
| *A61K 31/704* | (2006.01) |
| *A61K 41/00* | (2006.01) |
| *A61K 49/18* | (2006.01) |
| *A61K 31/00* | (2006.01) |
| *A61K 9/00* | (2006.01) |
| *A61K 9/51* | (2006.01) |

(52) U.S. Cl.
CPC ...... *A61K 47/48961* (2013.01); *A61K 9/0009* (2013.01); *A61K 9/5115* (2013.01); *A61K 31/00* (2013.01); *A61K 31/337* (2013.01); *A61K 31/704* (2013.01); *A61K 41/0028* (2013.01); *A61K 47/48861* (2013.01); *A61K 49/1857* (2013.01)

(58) Field of Classification Search
CPC ............ A61K 47/48961; A61K 31/337; A61K 31/704; A61K 47/48861; A61K 31/00; A61K 49/1857; A61K 9/0009; A61K 41/0028; A61K 9/5115
See application file for complete search history.

(56) References Cited

PUBLICATIONS

Benyettou et al., J. Mater. Chem. B., 2013, 1, 5076-5082.*
Wu et al., Nanomedicine (May 2015) 10(9), 1493-15-14.*

* cited by examiner

*Primary Examiner* — Robert Cabral
(74) *Attorney, Agent, or Firm* — Hodgson Russ LLP

(57) ABSTRACT

Provided are compositions and methods for transport, monitoring the transport, and controlled release of active agents. The compositions comprise surface functionalized iron oxide nanoparticles. The iron oxide nanoparticles are surface functionalized with cucurbitril[7] macrocycles. The cavity formed by the CB[7] macrocycles can be used for storage and transport of active agents. The active agents may be imaging agents or may be therapeutic agents which can be released by applying an alternating magnetic field at desired locations.

19 Claims, 35 Drawing Sheets

Figure 23: Table providing parameters for DFT Calculations

1: TPSSh/TZVP, 0 imaginary frequencies

| Center Number | Atomic Number | Coordinates (Angstroms) | | |
|---|---|---|---|---|
| | | X | Y | Z |
| 1 | 8 | 2.047047 | -4.042576 | -3.105306 |
| 2 | 8 | 1.731339 | -3.830062 | 3.129346 |
| 3 | 7 | 3.311092 | -4.225096 | -1.160946 |
| 4 | 7 | 1.245006 | -5.095383 | -1.189356 |
| 5 | 7 | 3.142877 | -4.062169 | 1.292631 |
| 6 | 7 | 1.164907 | -5.115426 | 1.275337 |
| 7 | 6 | 4.521740 | -3.640075 | -1.692155 |
| 8 | 1 | 4.416499 | -3.499260 | -2.747615 |
| 9 | 1 | 5.347442 | -4.292911 | -1.500005 |
| 10 | 6 | 2.177236 | -4.393225 | -1.951558 |
| 11 | 6 | 0.045910 | -5.629485 | -1.798238 |
| 12 | 1 | 0.030090 | -5.375462 | -2.837527 |
| 13 | 1 | 0.035265 | -6.694052 | -1.691071 |
| 14 | 6 | 3.213613 | -4.898249 | 0.112545 |
| 15 | 1 | 4.035632 | -5.624378 | 0.215846 |
| 16 | 6 | 1.798007 | -5.573058 | 0.061701 |
| 17 | 1 | 1.842400 | -6.673740 | 0.055078 |
| 18 | 6 | 4.286186 | -3.412359 | 1.891593 |
| 19 | 1 | 5.124949 | -4.076416 | 1.871470 |
| 20 | 1 | 4.059558 | -3.154623 | 2.905058 |
| 21 | 6 | 1.974649 | -4.265903 | 2.023861 |
| 22 | 6 | -0.080203 | -5.625556 | 1.799830 |
| 23 | 1 | -0.101330 | -6.690311 | 1.696146 |
| 24 | 1 | -0.164289 | -5.366220 | 2.834516 |
| 25 | 1 | -0.897505 | -5.198098 | 1.257431 |

Figure 23 (continued)

| 26 | 1 | 4.520626 | -2.524880 | 1.341758 |
| 27 | 1 | 4.697300 | -2.695070 | -1.222002 |
| 28 | 1 | -0.814305 | -5.213887 | -1.316357 |

E(RTPSSh) = -683.034335803 Hartree
Zero-point correction = 0.232730
Thermal correction to Energy = 0.247251
Thermal correction to Enthalpy = 0.248195
Thermal correction to Gibbs Free Energy = 0.191329
Sum of electronic and zero-point Energies = -682.808515
Sum of electronic and thermal Energies = -682.793995
Sum of electronic and thermal Enthalpies = -682.793050
Sum of electronic and thermal Free Energies = -682.849917

1 Fe(OH)3: TPSSh/TZVP, 0 imaginary frequencies

| Center Number | Atomic Number | Atomic Type | Coordinates (Angstroms) | | |
|---|---|---|---|---|---|
| | | | X | Y | Z |
| 1 | 8 | | -3.808151 | 0.211798 | 1.805822 |
| 2 | 8 | | 1.525283 | -0.282789 | -1.060089 |
| 3 | 7 | | -2.688410 | 1.175091 | 0.020797 |
| 4 | 7 | | -2.591503 | -1.048963 | 0.276408 |
| 5 | 7 | | -0.411971 | 0.986501 | -0.907306 |
| 6 | 7 | | -0.570909 | -1.230251 | -1.115475 |
| 7 | 6 | | -2.966209 | 2.555019 | 0.367758 |
| 8 | 1 | | -3.817396 | 2.552997 | 1.047819 |
| 9 | 1 | | -3.221223 | 3.119413 | -0.533102 |
| 10 | 6 | | -3.100186 | 0.125737 | 0.820331 |
| 11 | 6 | | -3.205280 | -2.323091 | 0.611978 |

Figure 23 (continued)

| 12 | 1 | -3.830080 | -2.155964 | 1.488754 |
| 13 | 1 | -3.830087 | -2.689349 | -0.212330 |
| 14 | 6 | -1.849641 | 0.748721 | -1.064069 |
| 15 | 1 | -2.188424 | 1.180178 | -2.012656 |
| 16 | 6 | -1.956682 | -0.807243 | -1.001783 |
| 17 | 1 | -2.544654 | -1.246154 | -1.816178 |
| 18 | 6 | 0.212017 | 2.278550 | -1.178605 |
| 19 | 1 | 0.172369 | 2.517494 | -2.247932 |
| 20 | 1 | 1.248712 | 2.242794 | -0.838101 |
| 21 | 6 | 0.282537 | -0.178163 | -1.009473 |
| 22 | 6 | -0.122151 | -2.608014 | -0.997584 |
| 23 | 1 | -0.753960 | -3.246384 | -1.618444 |
| 24 | 1 | 0.904778 | -2.655776 | -1.355896 |
| 25 | 1 | -0.149433 | -2.950544 | 0.039946 |
| 26 | 1 | -0.307446 | 3.052932 | -0.616371 |
| 27 | 1 | -2.119558 | 3.034238 | 0.868733 |
| 28 | 1 | -2.450688 | -3.073810 | 0.851245 |
| 29 | 26 | 3.109254 | -0.437666 | -2.375660 |
| 30 | 8 | 3.560006 | 1.332532 | -2.692476 |
| 31 | 8 | 4.301573 | -1.344050 | -1.294165 |
| 32 | 8 | 2.507205 | -1.359282 | -3.841513 |
| 33 | 1 | 2.787882 | -2.270345 | -3.986849 |

Figure 23 (continued)

| | | | | |
|---|---|---|---|---|
| 34 | 1 | 5.109251 | -0.899818 | -1.009785 |
| 35 | 1 | 3.490139 | 1.663369 | -3.596155 |

---

E(UTPSSh) = -2174.42932006 Hartree
Zero-point correction = 0.272029
Thermal correction to Energy = 0.295284
Thermal correction to Enthalpy = 0.296228
Thermal correction to Gibbs Free Energy = 0.216075
Sum of electronic and zero-point Energies = -2174.162308
Sum of electronic and thermal Energies = -2174.139052
Sum of electronic and thermal Enthalpies = -2174.138108
Sum of electronic and thermal Free Energies = -2174.218262

1···H2O Fe(OH)3: TPSSh/TZVP, 0 imaginary frequencies

| Center Number | Atomic Number | Coordinates (Angstroms) | | |
|---|---|---|---|---|
| | | X | Y | Z |
| 1 | 8 | 3.256666 | -2.358005 | -1.199067 |
| 2 | 8 | -0.264481 | 2.242425 | 0.337589 |
| 3 | 7 | 3.573193 | -0.176573 | -0.471638 |
| 4 | 7 | 2.013901 | -1.425941 | 0.530143 |
| 5 | 7 | 1.911091 | 1.620588 | -0.148574 |
| 6 | 7 | 0.815406 | 0.515331 | 1.451335 |
| 7 | 6 | 4.502122 | 0.214057 | -1.512376 |
| 8 | 1 | 4.979478 | -0.693166 | -1.880855 |
| 9 | 1 | 5.262077 | 0.880739 | -1.096935 |
| 10 | 6 | 2.969357 | -1.426187 | -0.469103 |
| 11 | 6 | 1.420135 | -2.661715 | 1.008426 |

Figure 23 (continued)

| | | | | |
|---|---|---|---|---|
| 12 | 1 | 1.760241 | -3.457327 | 0.345796 |
| 13 | 1 | 1.749421 | -2.881265 | 2.031542 |
| 14 | 6 | 2.922402 | 0.733550 | 0.430061 |
| 15 | 1 | 3.661268 | 1.321596 | 0.987247 |
| 16 | 6 | 2.060774 | -0.208487 | 1.317874 |
| 17 | 1 | 2.484929 | -0.401488 | 2.310297 |
| 18 | 6 | 2.248362 | 2.835296 | -0.870130 |
| 19 | 1 | 2.997307 | 3.420634 | -0.322522 |
| 20 | 1 | 1.335891 | 3.422263 | -0.966677 |
| 21 | 6 | 0.716398 | 1.512248 | 0.526969 |
| 22 | 6 | -0.307496 | 0.049330 | 2.254467 |
| 23 | 1 | 0.087853 | -0.399087 | 3.168108 |
| 24 | 1 | -0.917962 | 0.910970 | 2.524799 |
| 25 | 1 | -0.915880 | -0.673126 | 1.705998 |
| 26 | 1 | 2.632264 | 2.605698 | -1.865004 |
| 27 | 1 | 4.006309 | 0.711407 | -2.352721 |
| 28 | 1 | 0.330602 | -2.606477 | 0.978146 |
| 29 | 26 | 0.639627 | 6.013380 | 1.737017 |
| 30 | 8 | 0.646513 | 6.488211 | 3.501542 |
| 31 | 8 | 2.217377 | 5.178788 | 1.230941 |
| 32 | 8 | -0.135617 | 7.148253 | 0.496811 |
| 33 | 1 | -0.161132 | 8.107434 | 0.573599 |

Figure 23 (continued)

| 34 | 1 | 2.807037 | 4.922580 | 1.951903 |
| 35 | 1 | 0.006377 | 7.088466 | 3.899551 |
| 36 | 8 | -0.854100 | 4.607439 | 1.321549 |
| 37 | 1 | -1.423057 | 5.054159 | 0.678480 |
| 38 | 1 | -0.610579 | 3.714030 | 0.941028 |

---

E(UTPSSh) = -2250.89837472 Hartree
Zero-point correction = 0.296555
Thermal correction to Energy = 0.322557
Thermal correction to Enthalpy = 0.323501
Thermal correction to Gibbs Free Energy = 0.236098
Sum of electronic and zero-point Energies = -2250.607679
Sum of electronic and thermal Energies = -2250.581677
Sum of electronic and thermal Enthalpies = -2250.580733
Sum of electronic and thermal Free Energies = -2250.668136

(1)2···OH2: TPSSh/TZVP, 0 imaginary frequencies

| Center Number | Atomic Number | Coordinates (Angstroms) | | |
|---|---|---|---|---|
| | | X | Y | Z |
| 1 | 8 | -8.212428 | 0.168666 | 0.158505 |
| 2 | 8 | -2.246074 | -0.270446 | 1.172102 |
| 3 | 7 | -6.256476 | 1.207014 | -0.523798 |
| 4 | 7 | -6.282315 | -1.026936 | -0.350488 |
| 5 | 7 | -3.896692 | 1.034202 | 0.165762 |
| 6 | 7 | -3.825553 | -1.162601 | -0.252973 |
| 7 | 6 | -6.706062 | 2.570125 | -0.327067 |

Figure 23 (continued)

| | | | | |
|---|---|---|---|---|
| 8 | 1 | -7.795437 | 2.556673 | -0.319272 |
| 9 | 1 | -6.355383 | 3.197608 | -1.150534 |
| 10 | 6 | -7.045985 | 0.125232 | -0.189712 |
| 11 | 6 | -6.953128 | -2.299737 | -0.555983 |
| 12 | 1 | -7.979590 | -2.181673 | -0.210222 |
| 13 | 1 | -6.961015 | -2.578176 | -1.617948 |
| 14 | 6 | -4.909884 | 0.826525 | -0.864139 |
| 15 | 1 | -4.597988 | 1.314941 | -1.795282 |
| 16 | 6 | -5.000705 | -0.725029 | -0.968274 |
| 17 | 1 | -4.978425 | -1.100944 | -1.998564 |
| 18 | 6 | -3.256660 | 2.330049 | 0.346705 |
| 19 | 1 | -2.839921 | 2.697387 | -0.599695 |
| 20 | 1 | -2.451544 | 2.226519 | 1.073112 |
| 21 | 6 | -3.225487 | -0.139422 | 0.445168 |
| 22 | 6 | -3.475756 | -2.550616 | -0.028616 |
| 23 | 1 | -3.520406 | -3.098462 | -0.973228 |
| 24 | 1 | -2.457107 | -2.574993 | 0.356107 |
| 25 | 1 | -4.138795 | -3.029814 | 0.698961 |
| 26 | 1 | -3.975723 | 3.057652 | 0.724541 |
| 27 | 1 | -6.354535 | 2.989717 | 0.620917 |
| 28 | 1 | -6.472548 | -3.094240 | 0.016817 |
| 29 | 8 | -0.001514 | -0.382985 | 2.887280 |

Figure 23 (continued)

| | | | | |
|---|---|---|---|---|
| 30 | 1 | 0.769142 | -0.318940 | 2.311888 |
| 31 | 1 | -0.758727 | -0.469419 | 2.276033 |
| 32 | 8 | 2.256259 | -0.195352 | 1.201569 |
| 33 | 8 | 8.214482 | 0.254272 | 0.129054 |
| 34 | 7 | 3.678878 | 1.028282 | -0.159463 |
| 35 | 7 | 4.069275 | -1.161159 | 0.109323 |
| 36 | 7 | 6.134167 | 1.219678 | -0.262476 |
| 37 | 7 | 6.406580 | -0.969946 | -0.649494 |
| 38 | 6 | 3.136302 | 2.334357 | 0.152056 |
| 39 | 1 | 2.131570 | 2.185291 | 0.546007 |
| 40 | 1 | 3.084404 | 2.939901 | -0.756587 |
| 41 | 6 | 3.230605 | -0.114378 | 0.474098 |
| 42 | 6 | 3.590016 | -2.528492 | 0.212085 |
| 43 | 1 | 2.719250 | -2.516441 | 0.867087 |
| 44 | 1 | 3.296639 | -2.920912 | -0.770407 |
| 45 | 6 | 4.893334 | 0.805729 | -0.902839 |
| 46 | 1 | 4.816027 | 1.254427 | -1.901194 |
| 47 | 6 | 5.009236 | -0.747619 | -0.923353 |
| 48 | 1 | 4.733963 | -1.196766 | -1.885910 |
| 49 | 6 | 6.619387 | 2.586890 | -0.334830 |
| 50 | 1 | 6.553096 | 2.977769 | -1.358645 |
| 51 | 1 | 7.663505 | 2.575252 | -0.023259 |

Figure 23 (continued)

| | | | | |
|---|---|---|---|---|
| 52 | 6 | 7.047574 | 0.172975 | -0.212757 |
| 53 | 6 | 7.024273 | -2.275815 | -0.547580 |
| 54 | 1 | 6.756495 | -2.880869 | -1.417767 |
| 55 | 1 | 8.103245 | -2.126277 | -0.528393 |
| 56 | 1 | 6.727625 | -2.804813 | 0.364103 |
| 57 | 1 | 6.055331 | 3.240475 | 0.332502 |
| 58 | 1 | 3.732452 | 2.862553 | 0.903477 |
| 59 | 1 | 4.351194 | -3.181051 | 0.642747 |

---

E(RTPSSh) = -1442.54650780 Hartree
Zero-point correction = 0.491094
Thermal correction to Energy = 0.525415
Thermal correction to Enthalpy = 0.526359
Thermal correction to Gibbs Free Energy = 0.417252
Sum of electronic and zero-point Energies = -1442.064492
Sum of electronic and thermal Energies = -1442.030170
Sum of electronic and thermal Enthalpies = -1442.029226
Sum of electronic and thermal Free Energies = -1442.138333

COMPOSITIONS AND METHODS FOR IMAGING AND TREATMENT

CROSS-REFERENCE TO RELATED APPLICATIONS

This application claims priority to U.S. provisional patent application No. 62/033,249 filed on Aug. 5, 2014, the disclosure of which is incorporated herein by reference.

FIELD OF THE DISCLOSURE

The disclosure generally relates to nanoparticle compositions having multiple functionalities. More particularly, the disclosure relates to surface functionalized iron oxide nanoparticles which can be used for drug delivery, imaging and controlled release of cargo.

BACKGROUND OF THE DISCLOSURE

Cytotoxic drugs are often used to shrink primary tumors and prevent metastatic progression. However, these treatments are often systemic and not selective for cancer cells. Consequently, they must be injected in large doses to ensure that sufficient amounts reach the tumors. Because they are non-selective, they often kill healthy cells, resulting in serious side-effects. Biocompatible, non-toxic drug delivery systems have been developed; however, the FDA approved delivery systems, such as Abraxane®, Genexol-PM®, Doxil® and Onscaspar® serve only to improve the solubility of chemotherapeutic drugs. These delivery systems do not aid in targeting the drugs to tumors. Additionally, the diagnosis and imaging of tumor evolution remains a challenge.

The field of therapeutic diagnostics, or "theranostics", aims to provide therapeutic, diagnostic and preventative medical treatments that cause minimal side-effects. Theranostics is an area of personalized medical care, in which researchers are focused on the development of new nanomaterials that both treat and diagnose cancer. Nanoparticle-based theranostics aim to decrease drug dosage by concentrating the drugs in tumors, while simultaneously providing a means of tumor imaging. Magnetic NPs are already used clinically as a contrast agent for magnetic resonance imaging (MRI) (Endorem®, Sinerem®).

BRIEF SUMMARY OF THE DISCLOSURE

The present disclosure provides compositions and methods for delivery of drugs or other diagnostic or theranostic agents. The compositions comprise iron oxide nanoparticles surface functionalized with cucurbituril7 (CB[7]). Various agents can be loaded into the hydrophilic cavity of the CB[7] macrocycles. Compositions comprising drug loaded CB[7] functionalized iron oxide nanoparticles are stable and can be used for delivery and imaging applications.

The present disclosure also provides methods for making surface functionalized iron oxide nanoparticles and methods of using compositions comprising the particles. The surface functionalized particles may be prepared by contacting a colloidal suspension of iron oxide nanoparticles with an aqueous solution of CB[7]. The surface functionalized nanoparticles can then be loaded with desired cargo molecules.

The method of using the nanoparticles comprises introducing compositions comprising the nanoparticles into the circulation of an individual. The transport of the nanoparticles can be tracked using imaging systems—such as magnetic resonance imaging. The nanoparticles may be guided to desired locations by the use of magnets. At the desired locations, an alternating magnetic field may be used to effect an increase in temperature thereby causing release of cargo from the nanoparticles.

BRIEF DESCRIPTION OF THE FIGURES

FIG. 23 is a table showing parameters for computer aided DFT calculations for the compounds of FIG. 21.

DESCRIPTION OF THE DISCLOSURE

Figure 1:
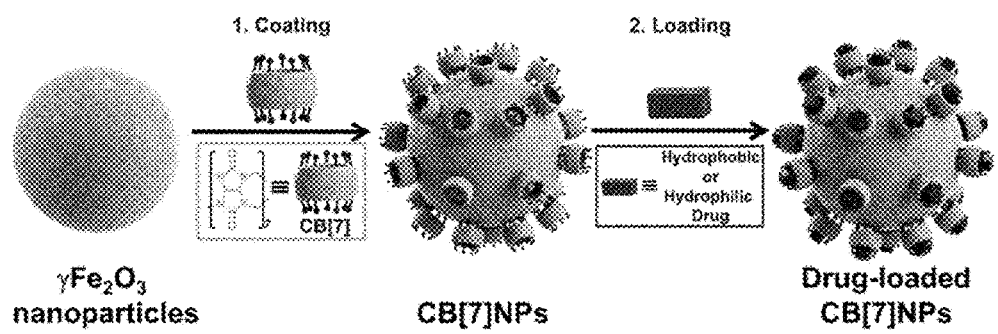
FIG. 1. Schematic representation of the synthesis of CB[7]NPs. The CB[7] macrocycles are adsorbed onto the surface of the nanoparticles (spheres), and then the macrocycles are loaded with one or more drugs that have affinity for the hydrophobic cavity of CB[7]. The drug-loaded CB[7]NPs may be encapsulated into peptides to improve specific cell targeting, e.g., cancer cells targeting.

The present disclosure provides iron oxide nanoparticles which are functionalized on the surface with water-soluble organic nanocontainers, such as cucurbituril[7](CB[7]). The CB[7] molecules are chemiadsorbed (chemisorbed) onto the surface (outer surface) of the iron oxide nanoparticles. The CB[7] adsorbed iron oxide nanoparticles are referred to herein as CB[7]NPs. Each CB[7] molecule (also referred to herein as CB[7] macrocycle) encloses a cavity which is generally hydrophobic. Therefore, CB[7] molecules can be loaded with one or more agents that have affinity for the hydrophobic cavity. The agents loaded into the CB[7] cavity may be referred to as cargo.

Cucurbiturils (CB[n]s) are a family of macrocycles that are synthesized by the condensation of 5, 6, 7, 8, or 10 glycouril subunits with formaldehyde under acidic conditions. Each CB [n] has two identical carbonyl-rimmed portals, a hydrophobic cavity that can hold neutral or cationic guest molecules, and an overall pumpkin-like shape.

The disclosure also provides compositions comprising the nanoparticles. The compositions may be used for delivery and/or tracking. The present disclosure also provides methods of making the nanoparticles and compositions and methods of using the nanoparticles/compositions. The nanoparticles are suitable for imaging, including MRI.

The CB[7]NPs can be used as drug delivery vehicles. The CB[7]NPs can act as imaging agents and are also heat-sensitive. Thus, the CB[7]NPs can be used as drug carriers, can be tracked by imaging, and can provide for controlled release of cargo under hyperthermic conditions. For example, the heat-sensitive CB[7]NPs enable delivery of anticancer drugs to tumors and allow for combined thermal and chemo-therapies. Controlled release of cargo is achieved by the application of an alternating magnetic field, which causes an increase in temperature. It is considered that the magnetic nanoparticles heat surrounding tissue by two different mechanisms: Néel relaxation, which involves rotation of magnetizations within the particles, and Brownian relaxation, which involves rotation of particles against the dispersed medium. Depending on the duration of the treatment and the temperature reached in the tumor, cancer cells are either immediately destroyed, a process known as thermal ablation, or weakened by the simultaneous use of chemotherapy and radiotherapy.

The CB[7] molecules are chemisorbed on to the surface of iron oxide nanoparticles. Free CB[7] macrocycles have carbonyl groups located on the two rims of the macrocycles. Upon interaction with iron oxide nanoparticles as described in the present disclosure, one or more of the carbonyl moieties on a rim of the CB[7] molecule interact (i.e., coordinate) with one or more iron atoms of a nanoparticle. This interaction leads to a stable iron oxide nanoparticle-CB[7] complex. When the CB[7] macrocycles are adsorbed on the iron oxide nanoparticles, the presence of uncomplexed and particle-bound carbonyl groups can be observed. Thus, the CB[7] macrocycles complexed to iron oxide particles have free carbonyl groups on one rim with carbonyl groups on the other rim being complexed to the iron oxide particle. The complex may be via hydrogen bonding in a multivalent fashion to surface hydroxyl groups, or, alternatively, via electrostatic and van der Waals interactions directly with $Fe^{3+}$ ions on the surface of the iron oxide nanoparticles. The supramolecular binding mode between Dox and CB[7] was assessed in solution using $^1H$ NMR experiments as well as computer-aided DFT calculations. The interaction of Dox with the carbonyl-rich portal of CB[7] on the surface of NPs was confirmed by Fourier transform infrared (FTIR) spectroscopy and thermogravimetric analysis. In one embodiment, the interaction of the CB[7] with the iron oxide particles does not involve catechols, carboxylates, or phosphonates. In one embodiment, the interaction of the CB[7] with iron oxide nanoparticles does not involve strong ionic and polar covalent bonds. The CB[7]-iron oxide nanoparticle assemblies are held together by weak reversible interactions, which make them particularly responsive to external stimuli in particular competitive agents and heat.

In various examples, CB[7] molecules are chemisorbed on at least 70%, 80%, 90%, 95%, 99% or 100% of the total surface area of the iron oxide nanoparticle. In one embodiment, the CB[7] molecules form a single layer on the surface of the nanoparticle (as illustrated in FIG. 1. An iron oxide nanoparticle may have from 1 to 30 (and all integer values therebetween) single-layered CB[7] molecules thereon. In various embodiments, the iron oxide nanoparticles may have 15-30 single-layered CB[7] molecules per nanoparticle. In one embodiment, there are approximately 700 atoms of iron in a nanoparticle.

The iron oxide nanoparticles are generally spherical and have a longest dimension (i.e., diameter) in the range of 5 nm to 15 nm. This represents the diameter of the iron oxide nanoparticles without taking into account the thickness provided by (CB[7]) molecules that are chemisorbed on to the surface.

A variety of drugs can be loaded on to CB[7]NPs. The drugs are generally located in the cavity of the CB[7] macrocycles. Any hydrophobic drug or any diagnostic, imaging or theranostic agent may be loaded. For example, anticancer drugs such as doxorubicin, cisplatin, paclitaxel, camptothecin, daunorubicin, alendronate, zoledronate and the like can be loaded on to the CB[7] NPs. These drugs were found to show a strong affinity for the cavity of the CB[7]. Results have shown that the encapsulation of these drugs in CB[7]NPs can be achieved using non-covalent bonding interactions. In one embodiment, more than one drug may be loaded. The CB[7]NPs can be used to deliver drugs into cancer cells. In one embodiment, diagnostic or imaging agents may be additionally or alternatively loaded into the cavity of the CB[7] macrocycles. For example, a MRI contrast agent (such as Nile red (NR) dye) can be loaded into the cavities of CB[7] macrocycles of CB[7]NPs.

In an aspect, the present disclosure provides compositions comprising iron oxide nanoparticles in the range of 5 to 15 nm, wherein the nanoparticles are surface functionalized by chemiadsorption of CB[7] macrocycles on the surface. The CB[7]NPs can be used for loading of various agents that are useful for imaging, tracking, diagnostics and/or therapeutics. The compositions may comprise the CB[7]NPs in suitable buffers or pharmaceutical carriers.

In one embodiment, the disclosure provides compositions comprising CB[7]NPs which are loaded with agents useful for imaging, tracking, diagnostics and/or therapeutics. The compositions may be in a dry form, in a diluted form, or in a concentrated form. For example, the nanoparticles may be loaded with an anticancer drug (such as doxorubicin) and/or an MRI contrast agent (such as Nile Red). In one embodiment, different nanoparticles may be loaded with different cargo molecules. In one embodiment, the same nanoparticle may be loaded with more than one cargo molecule. These compositions may be in a ready-to-use form, which can be used for administration to individuals.

CB[7]NPs loaded with cargo molecules in pharmaceutically acceptable carriers are suitable for administration to an individual. Such carriers are known in the art and may include, for example, normal saline, water, buffered water, isotonic aqueous solutions, glycine solutions and the like. The pharmaceutical carriers may also include proteins or glycoproteins for enhanced stability, including albumin, lipoprotein and globulin. The compositions are generally sterilized by conventional means. For example, the compositions may be sterilized by exposure to UV light. The individual may be a human being or a non-human animal. Thus the compositions of the present disclosure may be used for both human as well as for veterinary use.

In one embodiment, the composition comprises a plurality of CB[7]NPs in a carrier. For example, the carrier is a buffer at a physiological pH. In one embodiment, the pH of the carrier is from 2 to 9. In one embodiment, at least 70%, 80%, 90%, 95%, or 100% of the iron oxide nanoparticles have a diameter of 5 nm to 15 nm. It is desirable that the surface modified iron oxide nanoparticles in the composition have a narrow size distribution. In various embodiments, at least 70%, 80%, 90%, 95%, or 100% of the iron oxide nanoparticles have a diameter of 8 nm to 10 nm. When a single layer of CN[7] molecules is present on the iron oxide nanoparticles, the diameter is about 10 to 12 nm. Thus, in various embodiments, at least 70%, 80%, 90%, 95%, or 100% of the CB[7]NPs have a diameter of 10 nm to 12 nm The present compositions are stable in standard buffers (such as phosphate buffers, saline, phosphate buffered saline and the like) at a pH of from 2 to 9. The buffers or saline may contain serum also. There is no observable dissociation of CB[7] from the iron oxide nanoparticle for at least a few days or months. In one embodiment, there is no observable dissociation for up to a year, or at least a year. The compositions can be stored at room temperature or at refrigeration temperatures and all temperatures therebetween.

In an aspect the present disclosure provides methods of making the nanoparticles/compositions disclosed herein. The iron oxide nanoparticles may be prepared in micelles by oxidation of iron(II) as described in Motte et al., Faraday Discuss, 2011, 149, 211-225, which description in incorporated herein by reference. The iron oxide nanoparticles are also available commercially. The preparation is also described in the examples below. In general, iron oxide nanoparticles are prepared or can be obtained from commercial sources (such as Sigma-Aldrich).

The iron oxide NPs are then complexed with CB[7] by mixing the NPs and an excess of CB[7]. For example, the excess may be from 500 to 1,500 equivalents In one embodiment, the excess is 1000 equivalents. By "equivalents" is meant the number of molecules of CB[7] to iron oxide particles. Thus 1,000 equivalents means for one iron oxide nanoparticle, 1,000 molecules of CB[7] are used.

For example, the NPS may be mixed with CB[7] in an aqueous solution (e.g., buffer or water) at about room temperature (22 to 25° C.) at pH 2 to 3 for 12-24 hours Unbound (i.e., free) CB[7] can be removed by washing with water. It was also observed that repeated washing allows for formation of iron oxide nanoparticles having a single layer of CB[7] adsorbed thereon. For example, 2, 3, 4 or 5 washings can be carried out. The CB[7]NPs can be used to load agents (such as drugs) in the cavity of CB[7]. The drug and the CB[7]NPs can be mixed in a neutral (7.2 to 7.5, such as pH 7.4) aqueous environment and this results in the formation of inclusion complexes with the drugs in the cavity of CB[7]. In one embodiment, CB[7] macrocyles can be complexed to the iron-oxide nanoparticles using microwave heating. For example, a microwave irradiation of 2.45 GHz, 30 minutes can be used. The CB[7]NPs so formed were stable under a wide pH range (2-12).

The term "drug", also referred to herein as "active agent" as used herein means any agent and therefore includes agents that are useful for therapeutics, diagnostics, tracking, imaging or any other use, or combinations thereof.

Once drugs were encapsulated, the surface modification of the drug-loaded NPs can be evaluated by infrared (IR) spectroscopy and/or by measuring the surface charge zeta-potential using dynamic light scattering (DLS). UV-Vis spectroscopy and thermogravimetric analysis can be used to quantify drug loading and efficiency.

The compositions described herein may be used for delivery, imaging and controlled release of cargo. The present compositions are advantageously used when the stimuli chosen is unique to disease pathology. For example, the iron nanoparticles of the present disclosure can be used to exploit the pH and glutathione content of cancer cells. Further, the heat sensitivity of the supramolecular complex that forms between an active molecule, e.g., doxorubicin and the hydrophilic CB[7] results in a controlled drug delivery nanocarrier that can simultaneously act as a heat-mediator for hyperthermia treatments and a delivery vehicle for a therapeutic drug. For example, we achieved the delivery and release of Doxorubicin (Dox) by relying on, the acidic pH (5.4) and higher concentration of glutathione (2-10 mM) within tumors as internal stimuli and the heat induced by magnetic irradiation as an external stimulus. The loading and release of Dox in CB[7] on surface of NPs is pH- and glutathione (GSH)-level sensitive allowing for intracellular release of Dox within the acidic microenvironment of late endosomes and lysosomes. In addition, the release of Dox was found to be temperature dependent, hence, gradual release of drugs is possible by magnetically heating a drug loaded CB[7]NPs. The multiple-stimuli responsive system allows for combined therapies (hyperthermia and chemotherapy) coupled to diagnosis and has advantages to offer in cancer therapy over system that are single-stimulus responsive and do not achieve combines therapies.

The present compositions into which drug molecules have been loaded may be administered to an individual by routine techniques. For example, the composition may be introduced into the circulation of an individual. The compositions can be administered via standard delivery devices such as needles, catheters and the like. The administration may be carried out via any route including intravenous, oral route, infusion, subcutaneous, intramuscular route. The compositions may be administered over a suitable period of time as a continuous infusion or as multiple administrations or may be administered as a single injection.

The transport of the nanoparticles can be tracked by imaging—such as MRI. For this purpose, some of the nanoparticles may be loaded with MRI contrast agents—such as Nile Red. The nanoparticles may be guided to a desired location by the application of magnetic field (such as via magnets). The magnets may be placed insider or outside an individual's body. For example, a magnet can be placed externally but close to the tumor if it is not a deep tumor. Alternatively, a biocompatible magnet can be placed inside an individual's body in close proximity to the tumor.

Once the nanoparticles have reached their target, release of cargo can be achieved or enhanced by the use of an alternating magnetic field, which increases the temperature and results in release of cargo. An alternating current can be provided to an electromagnet, thereby creating an alternating magnetic field. Eddy currents are induced in the iron oxide particles when the particles are subjected to this alternating magnetic field, and heat is generated in the particles by the eddy currents.

FIG. 1 provides an illustration of the iron-oxide NPs. The iron-oxide NPs can be loaded with hydrophobic and/or hydrophilic agents. The particles can be magnetically guided to desired locations (such as tumors). Further, MRI contrast enhancement can also be achieved. In one embodiment, a dye (such as Nile red (NR) dye) can be loaded into the cavities of the surface-adsorbed CB[7]s. In other embodiments, different hydrophobic dyes may be loaded into the cavities of the surface adsorbed CB[7]s The loading of MRI contrast agents allows monitoring of the nanoparticles in vivo and also enables monitoring and intracellular delivery of the dye in vitro. For example, MRI contrast agent can be used to determine if the nanoparticles are being taken up by cancer cells (such as colon cancer cells HCT116). This can be observed, for example, by confocal laser scanning microscopy.

The present compositions can simultaneously target a specific site of pathology, monitor it by MRI, and treat the disease by controlling the gradual release of the delivered anti-cancer drug. The compositions of the present disclosure have multiple-purpose functionality (including drug delivery and magnetic resonance imaging) and can consolidate potent, non-toxic therapy with improved means of diagnosis. The present technology can be used for treating cancer in a relatively sensitive and selective manner.

In an embodiment, a method of making a composition comprises: a) providing a plurality of iron nanoparticles having a diameter of 5 nm to 15 nm in an aqueous medium; b) contacting the iron nanoparticles with at least a 700 excess equivalent of CB[7] (i.e., 700 molecules of CB[7] per iron oxide nanoparticle) such that a plurality of CB[7] molecules are chemisorbed on at least a portion of a surface of the iron nanoparticles to form surface-modified iron oxide nanoparticles; c) separating free CB[7] molecules from CB[7] molecules adsorbed on to the surface of the iron oxide NPs; d) contacting the CB[7] complexed iron nanoparticle with an agent which loads into the cavity of the CB[7] molecules; and removing free (i.e., unloaded) agent. In one embodiment, the excess equivalent of CB[7] to iron oxide nanoparticles is from 700 to 1,500. In one embodiment, it is about 1,000. In one embodiment, the iron oxide nanoparticles have a diameter of from 8-10 nm and after CB[7] molecules are adsorbed on the surface, the diameter is from 10-12 nm. The CB[7] complexed iron nanoparticles may have one or more targeting ligands complexed on the surface of the nanoparticles. Examples of suitable targeting ligands include folic acid, peptides and combinations thereof. The targeting ligands can be complexed to the surface of the nanoparticle by methods known in the art. In one embodiment, the chemisorbtion may be achieved by exposure to microwave radiation.

The compositions are useful for the treatment of various indications. For example, the compositions can be used for the treatment of any indication where a drug is desired to be delivered to cells, such as at a particular site. For example, this present compositions can be used for the treatment and/or diagnosis of cancer. By combining the ability to track the agent that is delivered, both diagnostic and therapeutic goals can be achieved with the same administration. The diagnostic aspects may involve tracking of the drug via imaging modalities.

In an embodiment, a method of delivering an active agent to an individual comprises: a) administering a CB[7]NP composition of the present disclosure to an individual; b) optionally tracking the nanoparticles and/or guiding the nanoparticles to one or more desired locations; and c) exposing the desired location to an alternating magnetic field such that the temperature of the nanoparticles is increased and at least a portion of the active agent is released from the CB[7] molecules. In an embodiment, the individual has magnetic material in a specific location inside the individual (e.g., a tumor in the individual) or in proximity to the individual and the individual is exposed the alternating magnetic field after a portion of the iron oxide nanoparticles accumulate in the specific location inside the individual. In an embodiment, the method further comprises obtaining imaging data (e.g., by magnetic resonance imaging) on the individual after administering the composition the individual and before exposing the individual to an alternating electric field to determine the movement, location, and/or status of the individual.

The present disclosure also provides kits comprising the compositions described herein. In one embodiment, a kit comprises one or more of the following: iron oxide nanoparticles which have chemiadsorbed on their surface a plurality of CB[7] macrocycles, one or more agents for loading in the cavity of CB[7] macrocycles, optionally, instructions for loading the agent and/or instructions for use, and suitable buffers.

The following examples are presented to illustrate the present invention. They are not intended to limiting in any manner.

Example 1

This example describes the preparation and characterization of surface modified iron oxide nanoparticles of the present invention. The materials and methods used for these studies are described toward the end of this example.

Figure 2:
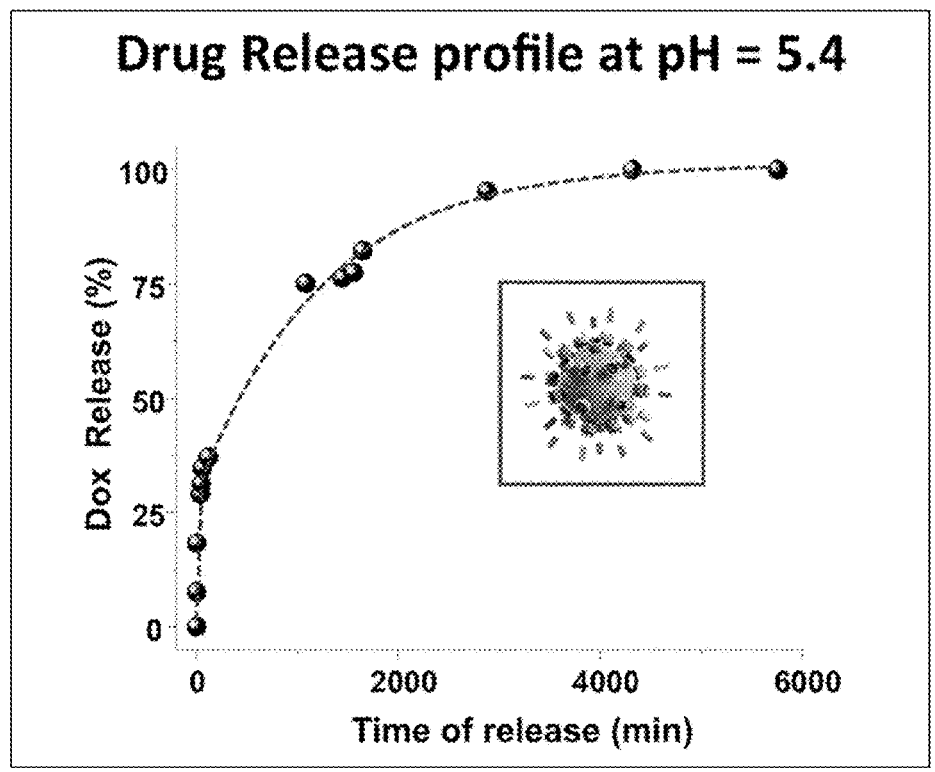
FIG. 2. In vitro doxorubicin (DOX) release profiles for DOX-loaded CB[7]NPs in PBS at 37° C. at pH 5.4.

Results of in vitro drug release profiles (FIG. 2) showed that only a small amount of the loaded DOX was released in PBS solution at pH 7.4, while up to about 95% of the loaded DOX could be released at pH 5.4 due to the pH-dependent disassembly of CB[7]NPs loaded with Doxorubicin. These results show that the release of the drugs is pH-dependent and can be triggered while in the cells.

Figure 3:
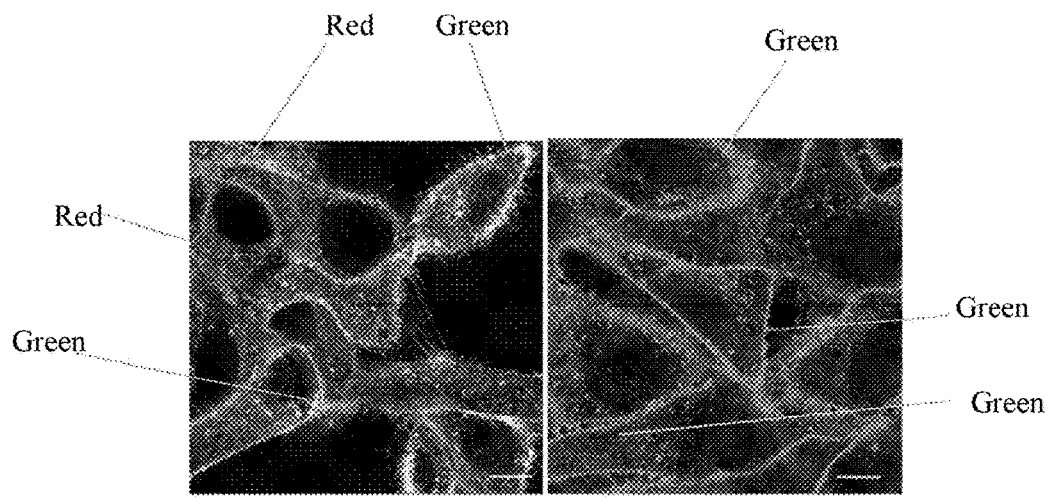
FIG. 3. Confocal images of Hela cells (a) incubated with DOX-loaded CB[7]NPs for 3 h at 37° C. and (b) with no NPs showing localization of nanoparticles inside the cell. The membrane is labelled in green.

In vitro biological assessment of the chemotherapeutic nanoplatform on cancer cells was done as follows. Cell internalization study was carried out using transmission electron microscopy (TEM) imaging studies. This allowed direct visualization of the intracellular localization of nanoparticles. Additionally, following incubation of the cells with the nanoparticles at two different temperatures (37° C. and 4° C.), fluorescence microscopy (FIG. 3) was used to determine whether cellular internalization is through an active or passive mechanism.

In vitro studies of the antitumor effect (6 Months) were carried out. The evaluation of the antitumor potential of our drug delivery system was performed in vitro on different relevant cell lines. We selected various tumor cell lines: MDAMB231 (breast cancer), HCT116 (colon cancer), HeLa (cervical cancer), CT26 (murine colon cancer), and LLC (lung cancer). These cell lines are commonly used as models in developing cancer therapies. Non-tumor cell lines such as macrophages and endothelial cells can also be studied to establish the specificity of these agents for cancer cells and their biocompatibility with healthy tissue.

Figure 4:
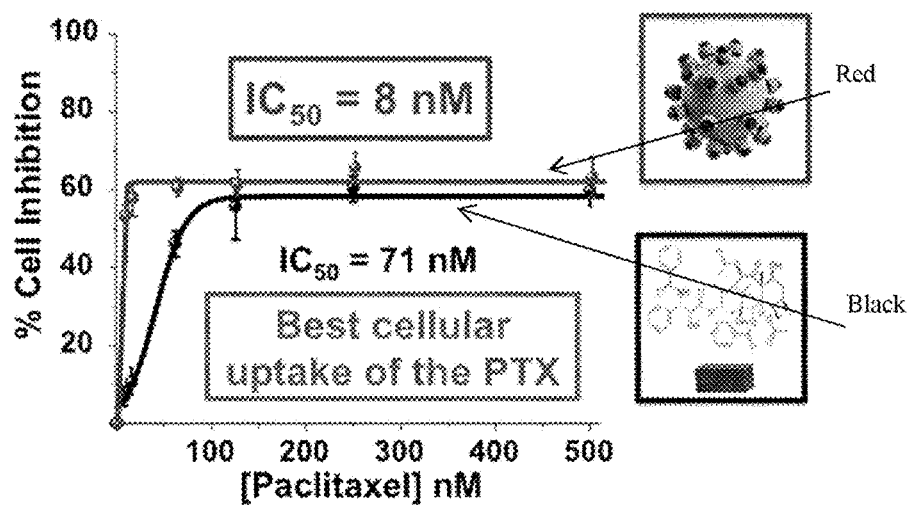
FIG. 4. Inhibition of HCT116 cell proliferation after 48 hours plotted against the concentration of paclitaxel (PTX). Black plot: free PTX, red plot: Paclitaxel-loaded CB[7]NPs.

Our studies show that CB[7]NPs efficiently deliver the Paclitaxel into cancer cells. After being functionalized, the physicochemical properties of the Paclitaxel-loaded CB[7] NPs were investigated (FIG. 4). In order to determine the antitumor properties of the Paclitaxel-loaded CB[7]NPs, the inhibition of cancer cell growth by free Paclitaxel and Paclitaxel-loaded CB[7]NPs was plotted against the concentration of Paclitaxel after 48 hours of incubation in the presence of HCT116 cells (FIG. 4). Free Paclitaxel inhibits the growth of HCT116 cells with an $IC_{50}$=71 nM (black curve). Loading PTX in the CB[7] cavities on the surface of the nanoparticles (red curve) enhances the anti-proliferative activity of the drug considerably ($IC_{50}$=8 nM). These results demonstrate that encapsulation of drugs in the CB[7] cavities on the NP surfaces facilitates the cellular internalization of the drug, thereby enhancing its anti-cancer properties. We show here that encapsulated drugs can be used to successfully delivering them into cancer cells, reducing the amount of drug necessary to induce the anti-cancer effect by an order of magnitude.

Diagnostic imaging in vitro: magnetic resonance imaging. The MRI contrast agent properties of our system can be demonstrated in vitro on the different cell lines incubated with NPs. This study can be performed using a micro MRI 7T (Bruker 300WB) dedicated to molecular MRI and allowing collecting 3D images with spatial resolution of 100 μm. The efficiency and stability of synthesized probes can be evaluated by relaxometry. MRI and micro MRI methods can be developed in vitro by 3D anatomical sequences, $T_1$ and $T_2$*-weighting, quantitative $T_1$ and $T_2$ mapping, susceptibility weighted imaging, to optimize the contrast and sensitivity threshold.

Iron oxide ($\gamma$-$Fe_2O_3$) nanoparticles (NPs) were coated with the water soluble macrocycle cucurbit[7]uril (CB[7]) by microwave heating. Density functional theory (DFT) calculations support a binding model in which the carbonyl oxygens of CB[7] coordinate directly to surface $Fe^{3+}$ ions. The modified particles (CB[7]NPs) are stable under a wide pH range (2-12) and have a transverse relaxivity, $R_2$, of 113 $s^{-1}$ $mM^{-1}$. Nile red (NR) dye was loaded into the cavities of the surface-adsorbed CB[7]s, and intracellular delivery of the dye to HCT116 cells was observed by confocal laser scanning microscopy. The dye-loaded particles (CB[7]NPsINR) have a $R_2$ of 172 $s^{-1}$ $mM^{-1}$. The stability, biocompatibility, and dual purpose functionality (drug delivery and magnetic resonance imaging) of the CB[7]NPs herald the theranostic potential of this system. Magnetic iron oxide nanoparticles (NPs) composed of g-$Fe_2O_3$ provide ultrasmall size, biocompatibility, and super-paramagnetism.

Figure 5:
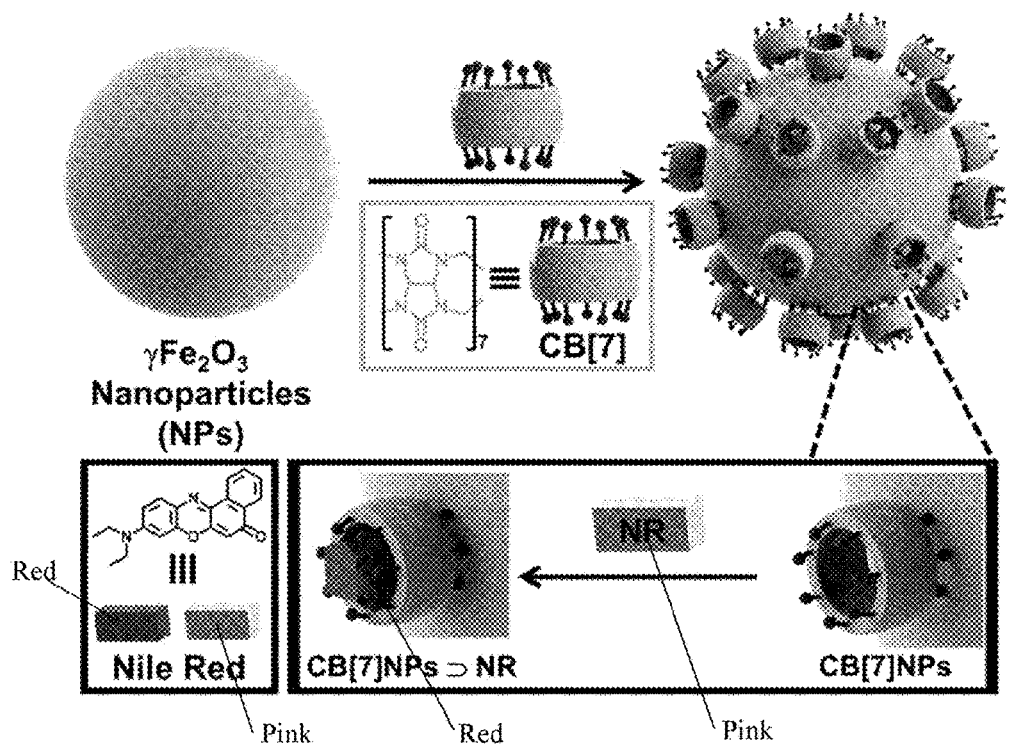
FIG. 5. Schematic representation of the synthesis of CB[7]NPs. The CB[7] macrocycles (bands) are adsorbed to the surface of iron oxide NPs (spheres). The capturing of water-quenched Nile Red (NR, pink block) by CB[7]NPs activates the dye's fluorescence (red block).

FIG. 5 provides an illustration of loading of the CB[7]NPs with an MRI contrast dye—Nile Red. We observed that that CB[7]NPs efficiently deliver the fluorophore Nile Red (NR) into HCT116 cells. A dual-function system provided in the present disclosure that has both imaging and drug-delivery capabilities, can serve as a theranostic agent—a medical tool used to treat and monitor disease simultaneously.

Figure 6:
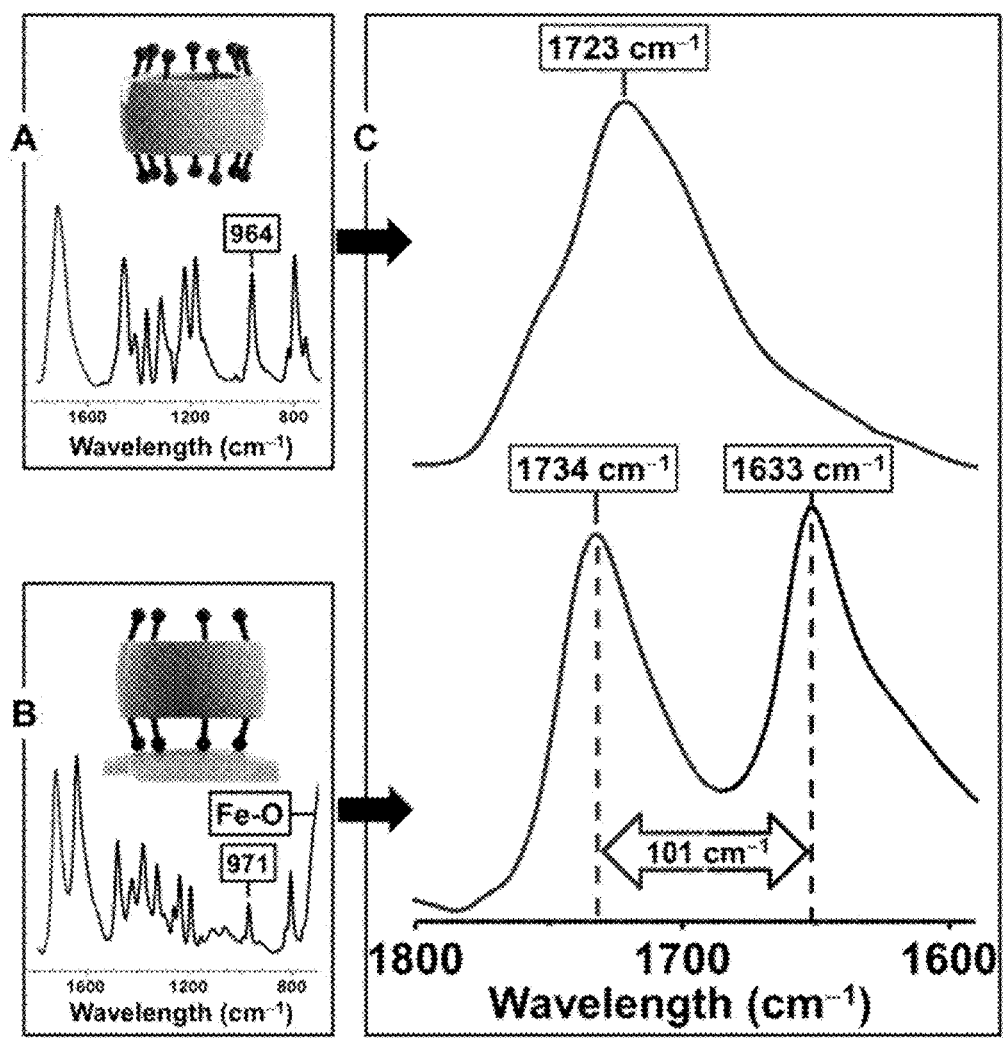
FIG. 6. Experimental FTIR spectra of free CB[7] (A) and CB[7]NPs (B) and an expanded and stacked plot of the two spectra (C) that shows the carbonyl absorption bands of each. The carbonyl groups (red) of free CB[7] are chemically equivalent by symmetry and give rise to a single IR absorption band at 1723 $cm^{-1}$. After complexation to NPs, the two rims of CB[7] are no longer equivalent. The carbonyl groups on one rim (red) extend outward into the solution and give rise to an absorption band at 1734 $cm^{-1}$, while those on the other side (blue) associate with the surface of the NPs and produce an absorption band at 1633 $cm^{-1}$.

Preparation of NPs & CB[7]NPs. NPs (8±1 nm in diameter) were prepared in direct micelles by oxidation of iron(II) in a basic medium. CB[7]NPs were first prepared by mixing NPs and an excess of CB[7] (1000 equivalents) in water at room temperature and pH=2 for 24 hours. Residual CB[7] was removed from the brown solid product by repeated washings (3×) with water. Infrared spectroscopic analyses of the prepared samples of NPs and CB[7]NPs reveal a vibrational absorption band at 580 $cm^{-1}$ that is characteristic of iron oxide nano-particles and corresponds to the Fe—O bond stretch. FIG. 6 shows Fourier transform infrared (FTIR) spectra of free CB[7] and CB[7]NPs. The band at 964 $cm^{-1}$ (FIG. 6A) in the spectrum of CB[7] and the band at 971 $cm^{-1}$ (FIG. 6B) in the spectrum of CB[7]NPs can be assigned to mixed vibrations involving C—C and C—N bonds of the CB[7] macrocycle and serve as a spectroscopic signature for CB[7] surface adsorption. The C=O bonds located on the two rims of the free CB[7] macrocycle are symmetrically disposed and give rise to a single vibrational band at 1723 $cm^{-1}$. In contrast, analysis of the nanoparticles modified with CB[7] reveals two prominent C=O stretching bands at 1734 and 1633 $cm^{-1}$ (FIG. 6C), a splitting which strongly suggests the presence of uncomplexed and particle-bound carbonyl groups, respectively. Although CB[7] lacks anchoring groups such as catechols, carboxylates, or phosphonates, that form strong ionic and polar covalent bonds with metal and metal-oxide surfaces, its carbonyl groups, which are significantly polar, are capable of hydrogen bonding in a multivalent fashion to surface hydroxyl groups, or, alternatively, of forming electrostatic and van der Waals interactions directly with $Fe^{3+}$ ions on the surface of the nanoparticles.

We analyzed the effect of conventional heating on the efficiency of grafting CB[7] to the surface of NPs. With the Fe—O absorption band used as a reference, we found that the IR spectra of CB[7]NPs prepared at 50° C. display C=O absorption bands of greater intensity, (see FIG. 12 D). This result confirms that the extent of surface coverage by CB[7] increases at higher reaction temperature. It is also well known that microwave heating can significantly increase the rates and yields of chemical reactions. When we performed reactions again at 50° C. and at the same concentrations of NPs and CB [7] but under microwave irradiation, successful grafting occurred in just 30 minutes (see FIG. 12E). The relative intensities of the C=O bands increased slightly after an additional 30 minutes of microwave heating (see FIG. 12F), but even after the first cycle, the bands were more intense than those observed after 24 hours of conventional heating. These data clearly show that the extent of NP surface coverage further increases with microwave heating and that the time needed for surface passivation can be greatly reduced from 24 hours to 1 hour.

The CB[7]NPs used in all of the studies described below were prepared by following the microwave-assisted procedure involving two 30 minute heating cycles.

Figure 7:
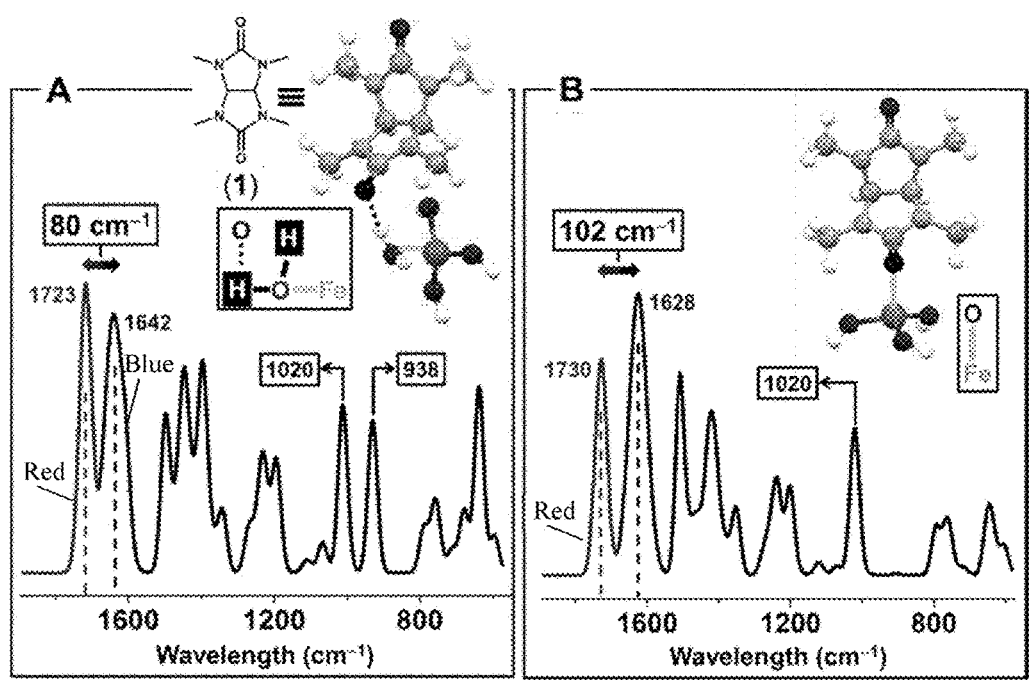
FIG. 7. Calculated FTIR spectra of model complexes 1 . . . ($H_2O$)Fe(OH)$_3$ (A) and 1-Fe(OH)$_3$ (B). The two carbonyl groups of 1 . . . ($H_2O$)Fe(OH)$_3$—one free, the other hydrogen bonded to water—produce absorption bands that are predicted to be 80 $cm^{-1}$ apart. The two carbonyl groups of 1-Fe(OH)$_3$—one free, the other directly bound to $Fe^{3+}$—are predicted to have absorption bands separated by 102 $cm^{-1}$, which is very close to the experimental value of 101 $cm^{-1}$. DFT calculations were performed at the TPSSh/TZVP level of theory.
Figure 21:
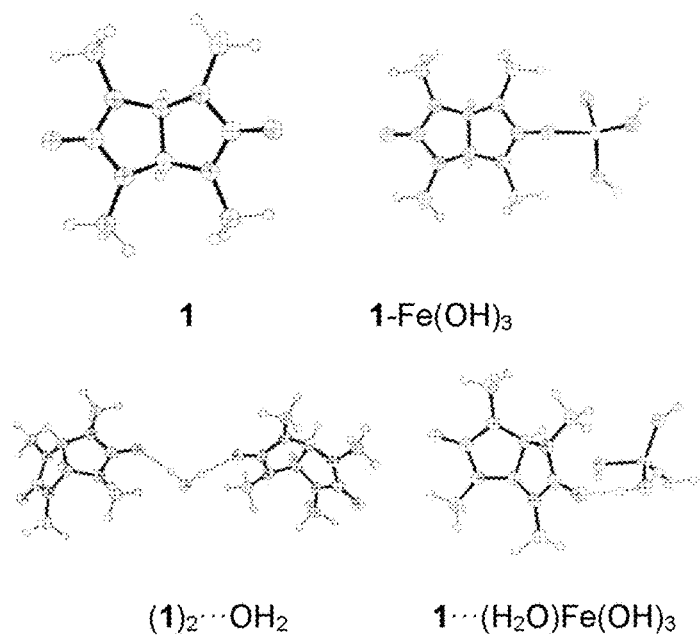
FIG. 21. Geometries of the model systems obtained by using DFT calculations (TPSSh/TZVP).
Figure 22:
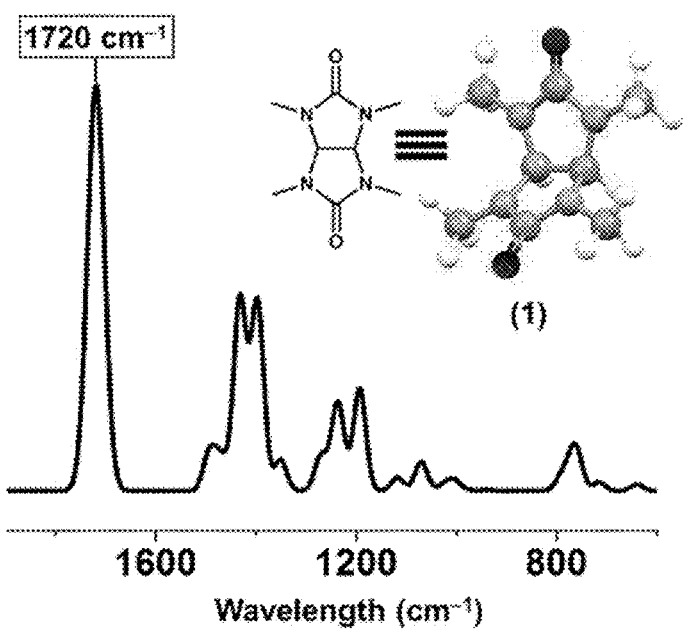
FIG. 22. Representation of the calculated FTIR spectrum of (1) used as a model for CB[7].

Density functional theory (DFT) calculations. To further elucidate the interactions between CB[7] and NPs, we performed DFT calculations at the TPSSh/TZVP level of theory (FIG. 23). To simplify the calculations, we used compound 1 (FIG. 7) as a model for CB[7]. Geometry optimizations of 1 and subsequent frequency calculations predict a single carbonyl absorption band at 1720 $cm^{-1}$ (FIG. 22), which is in excellent agreement with the experimental FTIR value of 1723 $cm^{-1}$. To model the surface of the nanoparticles, we used $Fe(OH)_3$ and $(H_2O)Fe(OH)_3$ complexes and considered two different interactions with 1: (i) 1 . . . $(H_2O)Fe(OH)_3$ (FIG. 7A) in which 1 forms a hydrogen bond to an iron-bound water molecule, with H-bonding represented by . . . , and (ii) 1-$Fe(OH)_3$ (FIG. 7B) in which 1 is directly bound to iron. In both cases $Fe^{3+}$ is tetrahedrally coordinated to three hydroxide ligands, and the coordination sphere is completed by either a water molecule as in . . . $(H_2O)Fe(OH)_3$ or a carbonyl oxygen atom of 1 as in 1-Fe$(OH)_3$ (FIG. 21) We obtained mean Fe—OH distances of 1.845 and 1.847 Å for 1/$(H_2O)Fe(OH)_3$ and 1-$Fe(OH)_3$, respectively. These values are close to the Fe—O distance of the tetrahedral sites in $\gamma$-$Fe_2O_3$ (1.803 Å). The Fe—$OH_2$ distance in 1 . . . $(H_2O)Fe(OH)_3$ (2.096 Å) is longer than the Fe—O carbonyl distance in 1-$Fe(OH)_3$ (2.049 Å), a difference which indicates a stronger Fe—O interaction in the latter case. Frequency calculations performed on 1 . . . $(H_2O)Fe(OH)_3$ and 1-$Fe(OH)_3$ provided the IR spectra shown in FIG. 7.

Each spectrum displays two carbonyl bands—at 1723 and 1642 $cm^{-1}$ for 1 . . . $(H_2O)Fe(OH)_3$ and at 1730 and 1628 $cm^{-1}$ for 1-$Fe(OH)_3$. The band at 1642 $cm^{-1}$ corresponds to the hydrogen-bonded carbonyl, whereas the band at 1628 cm$^{-1}$ represents the carbonyl that is directly coordinated to Fe$^{3+}$. For 1 . . . (H$_2$O)Fe(OH)$_3$, the difference in wavenumbers between the two absorptions is 80 cm$^{-1}$, whereas, for 1-Fe(OH)$_3$, the difference is 102 cm$^{-1}$ and is in much closer agreement with the experimentally determined value of 101 cm$^{-1}$. Furthermore, the calculated IR spectrum of 1 . . . (H$_2$O)Fe(OH)$_3$ shows two bands with maxima at 938 and 1020 cm$^{-1}$, whereas the calculated spectrum of 1-Fe(OH)$_3$ (FIG. 7B) and the experimental spectrum of CB[7]NPs (FIG. 6B) each show only one band in the 900-1100 cm$^{-1}$ region and are therefore more consistent.

We attribute the band at approximately 1020 cm$^{-1}$ to a combined vibration of C—C and C—N bonds in CB[7], and the band at 938 cm$^{-1}$ to the FeOH bending mode. Because the band at 938 cm$^{-1}$ is not observed in the calculated spectrum of 1-Fe(OH)$_3$, nor is there a corresponding band in the experimental spectrum of CB [7]NPs, we infer a lack of hydrogen-bonding interactions involving the oxygen atoms of CB[7] and OH groups on the surface of the nanoparticles. Although these in silico results must be considered with great care due to the complexity of the actual system and the simplicity of the models used, they suggest that CB[7] interacts with the g-Fe$_2$O$_3$ surface via direct coordination of the carbonyl groups of CB[7] to Fe$^{3+}$ ions.

Figure 13:
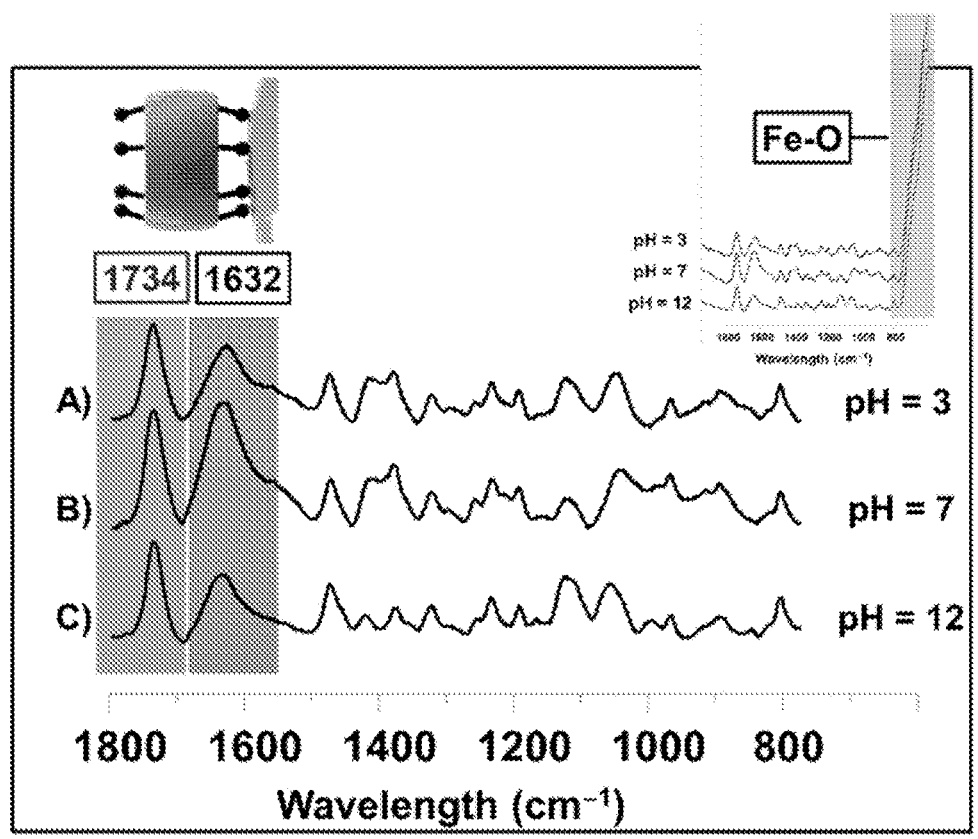
FIG. 13. FTIR spectra (800-1800 cm$^{-1}$) of CB[7]NPs at A) pH=3 B) pH=7 and C) pH=12. Inset: FTIR spectra (600-1800 cm$^{-1}$) of CB[7]NPs at different pH that display the Fe—O bond used as a reference. The three spectra were normalized using the Fe—O bond.

Chemical stability, high resolution transmission electron microscopy (HRTEM) and powder X-ray diffraction (PXRD). CB[7]NPs were initially synthesized in and isolated from aqueous solution at pH=2. The stability of the coordination between CB[7] and NPs was further tested by suspending CB[7] NPs in solutions of various pH (3, 7 and 12). After 24 hours, samples of CB[7]NPs from these solutions were magnetically separated from any dissociated CB[7]. The samples were then dried and analyzed by FTIR. In the spectra of all of these samples, the relative intensities and positions of the two C=O absorption bands that correspond to, respectively, the complexed and uncomplexed rims of CB[7] are unchanged (FIG. 13). The chemical stability demonstrated by this experiment is consistent with the presence of strong coordination bonds between the oxygen atoms of CB[7] and the Fe$^{3+}$ ions on the surface of the NPs.

Figure 8:
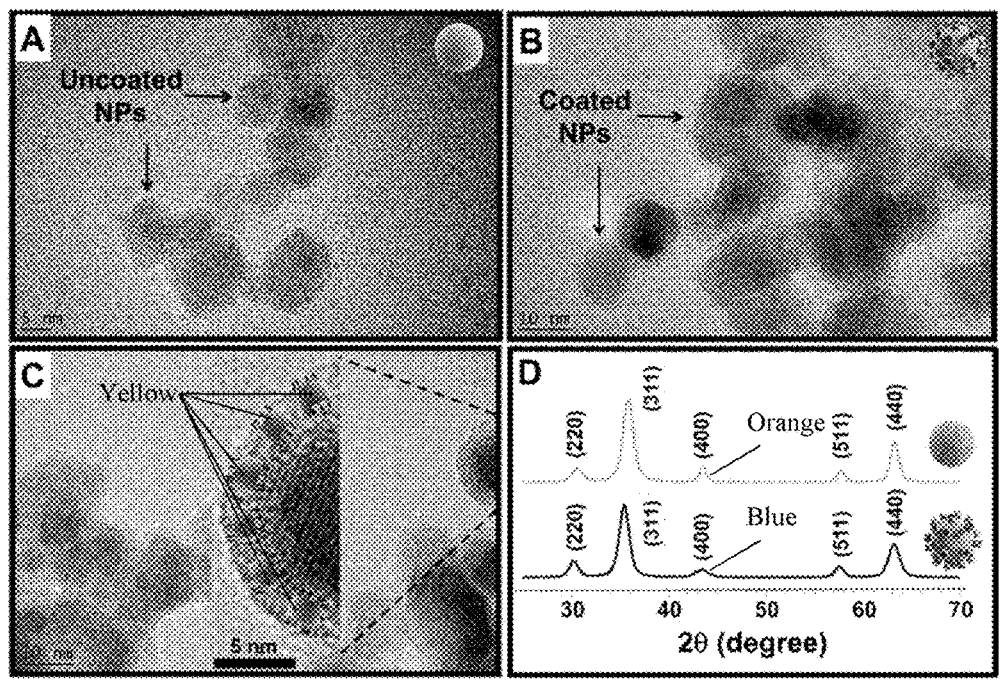
FIG. 8. High resolution transmission electron microscopy (HRTEM) images of NPs (A) and CB[7]NPs (B, C) and a stacked plot of the nearly identical PXRD patterns of NPs (orange) and CB[7]NPs (blue). In the inset of C, overlaid illustrations of CB[7] macrocycles (yellow bands) highlight the consistency between the thickness of the bright nominal layer on the surface of CB[7]NPs and the height of the macrocycles themselves.

High resolution transmission electron microscopy (HR-TEM) images (FIG. 8 and FIG. 14) show that the functionalization of NPs by CB[7] does not appreciably affect the size or shape of the nanoparticles. However, differences are discernible. The surfaces of uncoated nanoparticles appear free of any amorphous layer. Their lattice fringes always terminate at their surfaces (FIG. 8A), and no film coating is present. In contrast, the surface of CB[7]NPs has a continuous bright layer of approximately 1 nm thickness (FIGS. 8B and C) that can be attributed to a monolayer of CB[7]. (CB[7], itself, has a height of about 1 nm.).

The crystalline structures of NPs and CB[7]NPs were further characterized (FIG. 8D) by powder X-ray diffraction (PXRD). All the diffraction peaks can be indexed to cubic structures of Fe$_3$O$_4$/γ-Fe$_2$O$_3$. From the full width at half maximum (FWHM) for peak (311) and application of the Scherrer equation, the mean crystallite diameters of the nearly spherical particles were estimated to be 7.1±0.1 nm and 7.4±0.1 nm for NPs and CB[7] NPs, respectively. These values are in good agreement with the 8±1 nm value determined by TEM.

Figure 9:
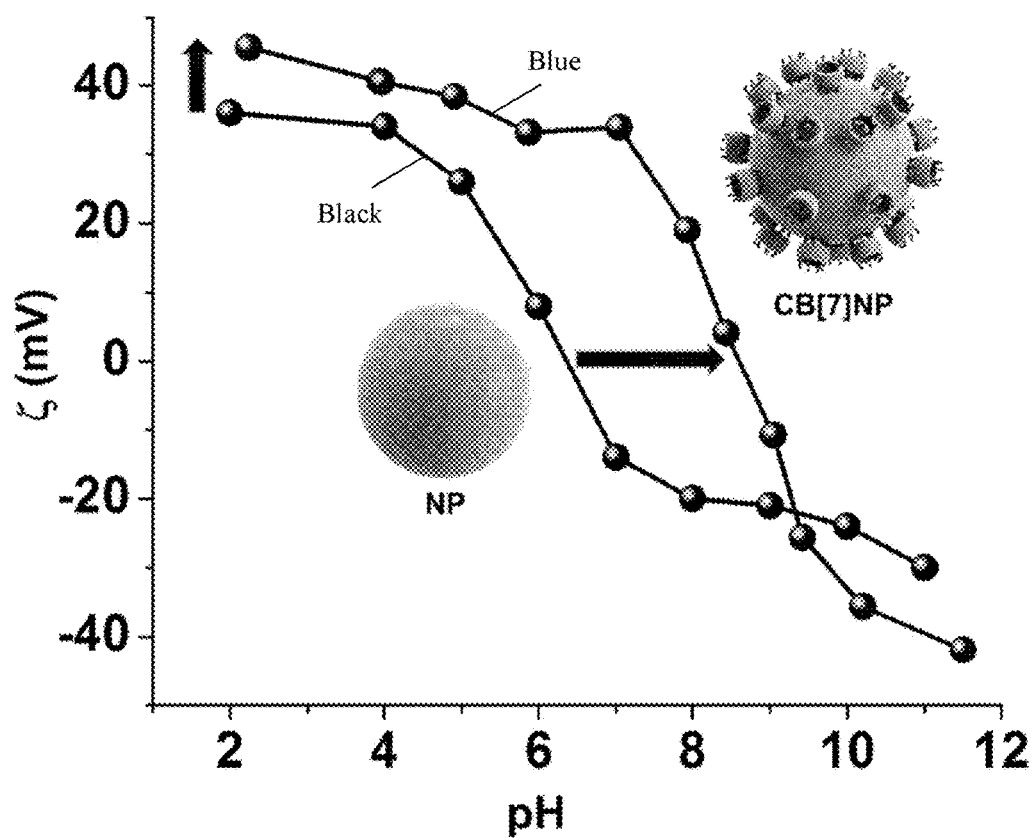
FIG. 9. Graphical illustration of the influence of pH on the ζ-potentials of NPs and CB[7]NPs. In aqueous solutions of pH 2 to ~9, the ζ-potential values of the CB[7]NPs (blue trace) are higher than of those of the NPs (black trace).

Zeta(z)-potential and dynamic light scattering (DLS). To investigate the electrostatic effects of CB[7], we measured the z-potentials of the nanoparticles before and after functionalization (FIG. 9). The ζ-potentials of NPs were +35 mV at pH 2, 0 mV at pH 6.7 (which corresponds to the isoelectric point, IEP) and −30 mV at pH 12. These data are consistent with the fact that, on the surface of uncoated NPs, the coordination spheres of Fe$^{3+}$ cations are completed by either hydroxyl/hydronium groups or by adsorbed water molecules. Surface functionalization with CB[7] resulted in a larger ζ value (+45 mV) at pH 2 and a shift of the IEP to higher pH (ζ ¼ 0 mV at pH 8.7). This is consistent with the outer surface of the CB [7] macrocycle being somewhat positive. A ζ value of −40 mV was measured at pH 12. Thus, in solutions that have pH values between 2 and ~8.5, CB[7]NPs have higher positive z-potentials than NPs, which is consistent with increased electrostatic repulsions between the particles and decreased aggregation.

DLS measurements of NPs and CB[7]NPs at pH 2 reveal relatively small hydrodynamic diameters (d) of 33 nm and 23 nm, respectively. These values are consistent with the outer surfaces of both types of nanoparticles being positively charged ($\zeta_{NPs}$=+35 mV and $\zeta_{CB[7]NPs}$=+45 mV). In this state, electrostatic repulsions counteract van der Waals attractions and minimize agglomeration. At most pH values (2 to 9) CB[7]NPs have smaller d values because they are more positively charged (i.e. have greater ζ values). For example, at pH=7, NPs (which have an IEP=6.7) are nearly neutral and strongly agglomerated (d~5590 nm), whereas CB[7]NPs have a surface charge of ~+35 mV and show significantly less agglomeration (d=43 nm), a comparable amount, in fact, to that observed for the commercial MRI contrast agent Resovist® (d=43.0±7.2 nm).

Surface quantification of CB[7]. Thermo-gravimetric analysis (TGA) was employed (35-700° C.) to determine the number of CB[7] molecules on the surface of CB [7]NPs. A composition of 94.84% iron oxide and 4.33% CB[7] (Table 1 and FIG. 16) was determined and corresponds to an average of twenty seven CB[7] macrocycles per nanoparticle, or, in other words, nearly quantitative surface coverage.

Figure 16:
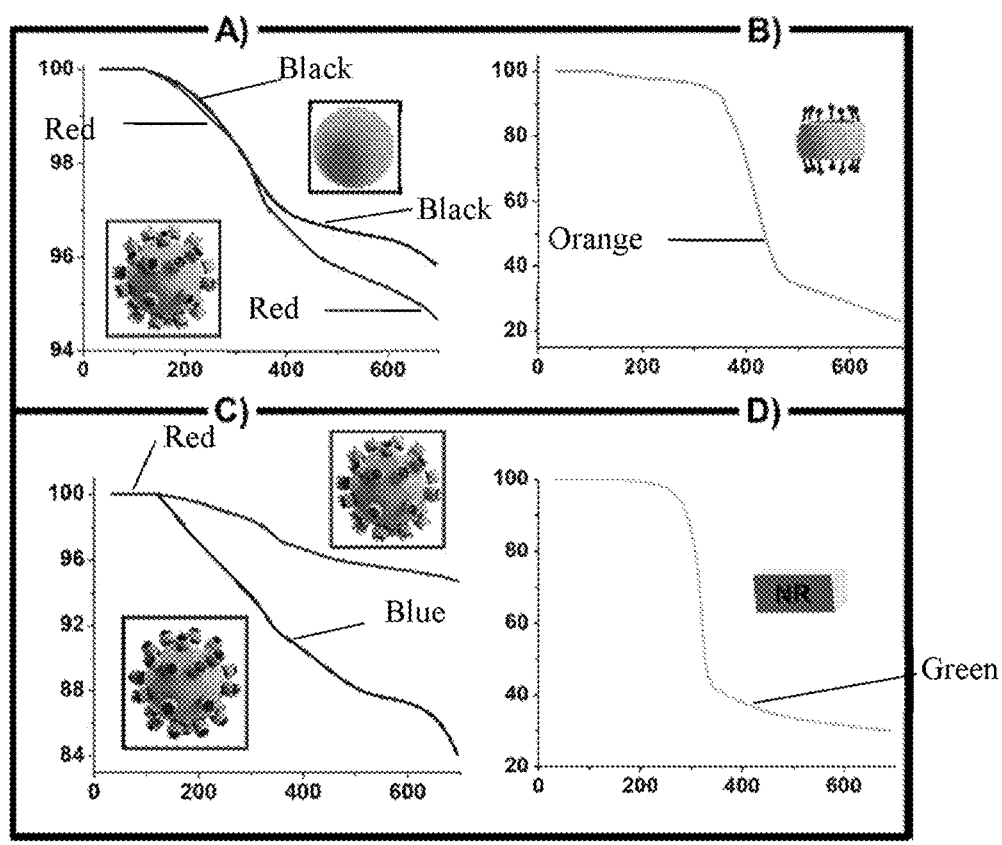
FIG. 16. TGA curves of A) NPs (black curve) and CB[7]NPs (red curve), B) CB[7] (orange curve). C) CB[7] NPs (red curve) and CB[7]NPs ⊃ NR (blue curve) and D) NR (green curve).

Encapsulation of Nile Red (NR). Having established the presence of CB[7] on the surface of NPs, we investigated the ability of CB[7]NPs to encapsulate molecules inside the cavity of CB[7]. We chose Nile Red (NR), a hydrophobic dye, for proof-of-principle experiments. NR's fluorescence is completely quenched in water; however, the dye emits red fluorescence in hydrophobic environments, such as the internal cavity of CB[7] (FIG. 16).

Figure 10:
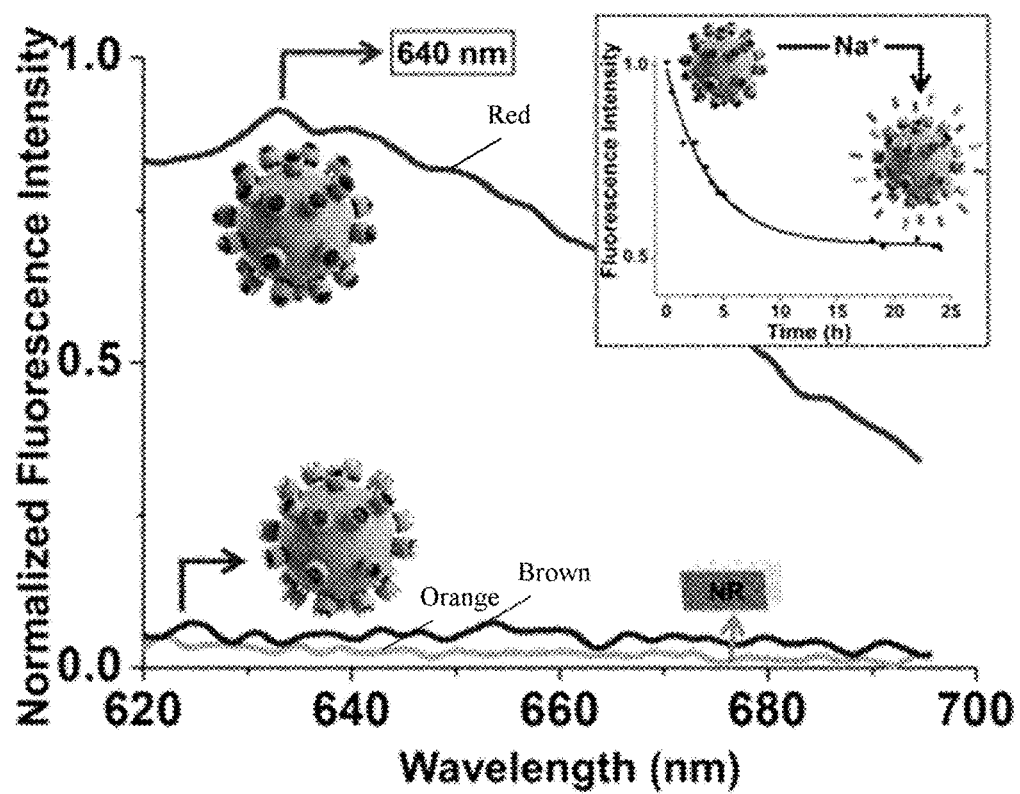
FIG. 10. Fluorescence emission spectra of CB[7] NPs⊃NR, NPs, and NR. In $H_2O$, CB[7]NPs⊃NR exhibit fluorescence (red trace) that is characteristic of NR when NR is in a hydrophobic environment. In the absence of CB[7] NPs, NR's fluorescence (orange trace) is completely quenched in $H_2O$, and CB[7]NPs alone do not fluoresce (brown trace) upon irradiation. These measurements were made (pH=7) at room temperature and by using an excitation wavelength of 510 nm, [NR]=[CB[7]]=8×10$^{-6}$ M. The inset shows the decrease in fluorescence intensity over time that occurs upon addition of Na$^+$ ions (in the form of NaOH or NaCl) to an aqueous solution of CB[7]NPs ⊃ NR.
Figure 12:
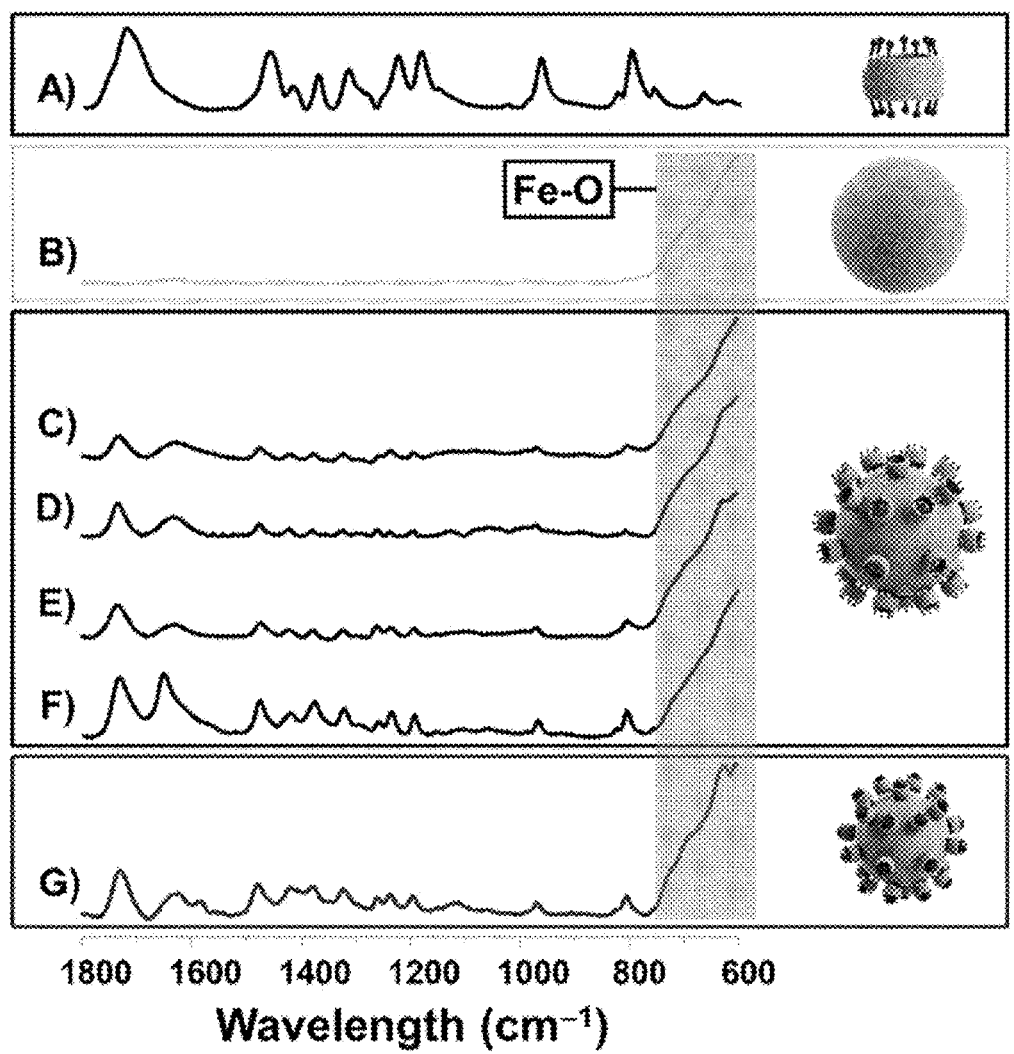
FIG. 12. FTIR spectra of A) CB[7] B) uncoated γ-Fe$_2$O$_3$ nanoparticles, NPs C) CB[7]NPs synthesized at room temperature for 24 hours D) CB[7]NPs synthesized by conventional heating at 50° C. for 24 hours E) CB[7]NPs synthesized by microwave heating at 50° C. for 30 minutes F) CB[7]NPs synthesized by microwave heating at 50° C. for 2×30 minutes and G) CB[7]NPs ⊃ NR.

Equimolar amounts of NR and CB[7]NPs were mixed in neutral aqueous solutions to test for the formation of the inclusion complex, CB[7]NPsINR. Evidence for the presence of NR in the cavity of CB[7] was provided by FTIR spectroscopy which shows absorption bands characteristic of NR in addition to those of CB[7] (FIG. 12). Additional evidence for the formation of CB[7]NP⊃NR came from fluorescence measurements (FIG. 10) which show the characteristic emission for CB[7] INR with $l_{max}$ ¼ 640 nm. Furthermore, the addition of NaCl decreased the emission intensity of the samples, an effect that can be explained by the competitive binding of sodium ions to the carbonyl portal of CB[7]. The binding of sodium ions displaces NR into solution and quenches the dye's fluorescence (FIG. 10, inset).

The presence of NR in the cavity of CB[7] of CB[7]NPs affects both the ζ potential (see FIG. 15) and the hydrodynamic diameter of the particles. Although the surface charges of CB[7] NPs ⊃ NR and CB[7]NPs at pH 2 are both positive (ζ=+35 mV and +45 mV, respectively), CB[7] NPs ⊃ NR exhibit a much larger hydrodynamic diameter (295 nm versus 23 nm) because of the hydrophobic attractions between dye molecules. The same is true at pH 7 at which their surface charges are +20 mV and +32 mV, respectively, and their corresponding hydrodynamic diameters are 436 nm and 44 nm, respectively. Also, at pH 7, CB[7]NPs ⊃ NR are more agglomerated, but are much less so than NPs whose hydrodynamic diameter is 5590 nm.

In order to test the behavior of CB[7]NPs ⊃ NR and to assess their stability in the presence of serum proteins, CB[7]NPs ⊃ NR were incubated for 24 hours in fetal bovine serum at room temperature. CB[7]NPs ⊃ NR were then magnetically separated and washed thoroughly with water. The fluorescence of the obtained nanoparticles was then recorded in water and showed no significant decrease in emission intensity as compared to those nanoparticles that were measured at the same concentration but had not been incubated in serum. Moreover, the hydrodynamic diameter (Table 2) of CB[7]NPs ⊃ NR in the serum was measured and found to be d=25.17 nm, which is much less than the 436 nm value obtained in pure water. This decrease can be explained by the extra stabilization that CB[7]NPs ⊃ NR acquire as a consequence of interactions with serum proteins that minimize inter-particle hydrophobic attractions between encapsulated NR dye molecules. These results suggest an additional strategy to minimize agglomeration and promote cellular uptake: the covalent linkage of large molecules such as peptides and polyethylene glycols to the surface of the nanoparticles.

Magnetic properties. Magnetic properties of NPs, CB[7] NPs, and CB[7]NPs ⊃ NR were determined (Table 3) at pH 7 using a MIAtek reader. CB [7]NPs and CB[7]NPs ⊃ NR present a more intense signal than NPs as a consequence of the low stability (strong agglomeration) of NPs at pH 7.

Figure 19:
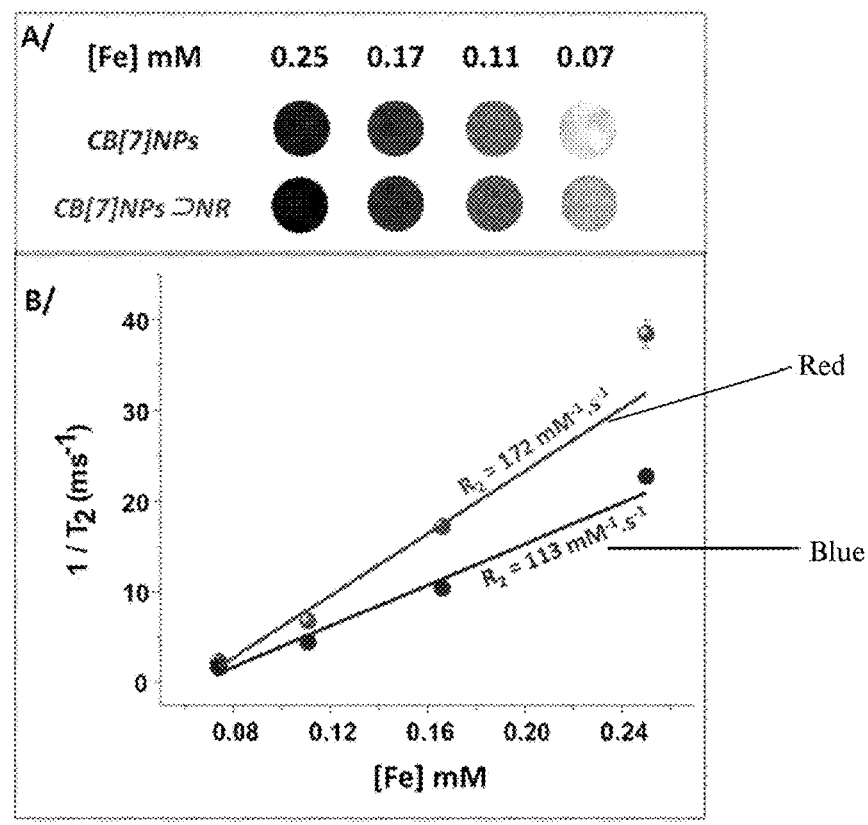
FIG. 19. T$_2$ weighted MR images of aqueous solutions of A) CB[7]NPs and CB[7]NPs ⊃ NR at various iron concentrations ([Fe]) and B) T$_2$ relaxation rates (1/T$_2$) plotted against the [Fe] for the various aqueous solutions of CB[7] NPs (blue) and CB[7]NPs ⊃ NR (red).

Magnetic resonance imaging (MRI) was performed using a 1.5T MR scanner. The transverse nuclear relaxation times, $T_2$, of NPs and CB[7]NPs vary linearly (FIG. 19) with iron concentration. The transverse relaxivity, $R_2$, of the CB[7] NPs (113 mM$^{-1}$s$^{-1}$) is similar to those of commercial MRI contrast agents such as Endorem® from Guerbet (98 mM$^{-1}$s$^{-1}$) and Resovist® from Bayer Healthcare (151 mM$^{-1}$s$^{-1}$) and suggests that CB[7]NPs, themselves, could be useful as MRI contrast agents. The presence of the dye slightly increases $R_2$ to 172 mM$^{-1}$s. This rise can be explained by the increased aggregation of CB[7]NP ⊃ NR versus CB[7]NPs and the fact that cooperative magnetic behavior is induced when individual particles aggregate.

Figure 11:
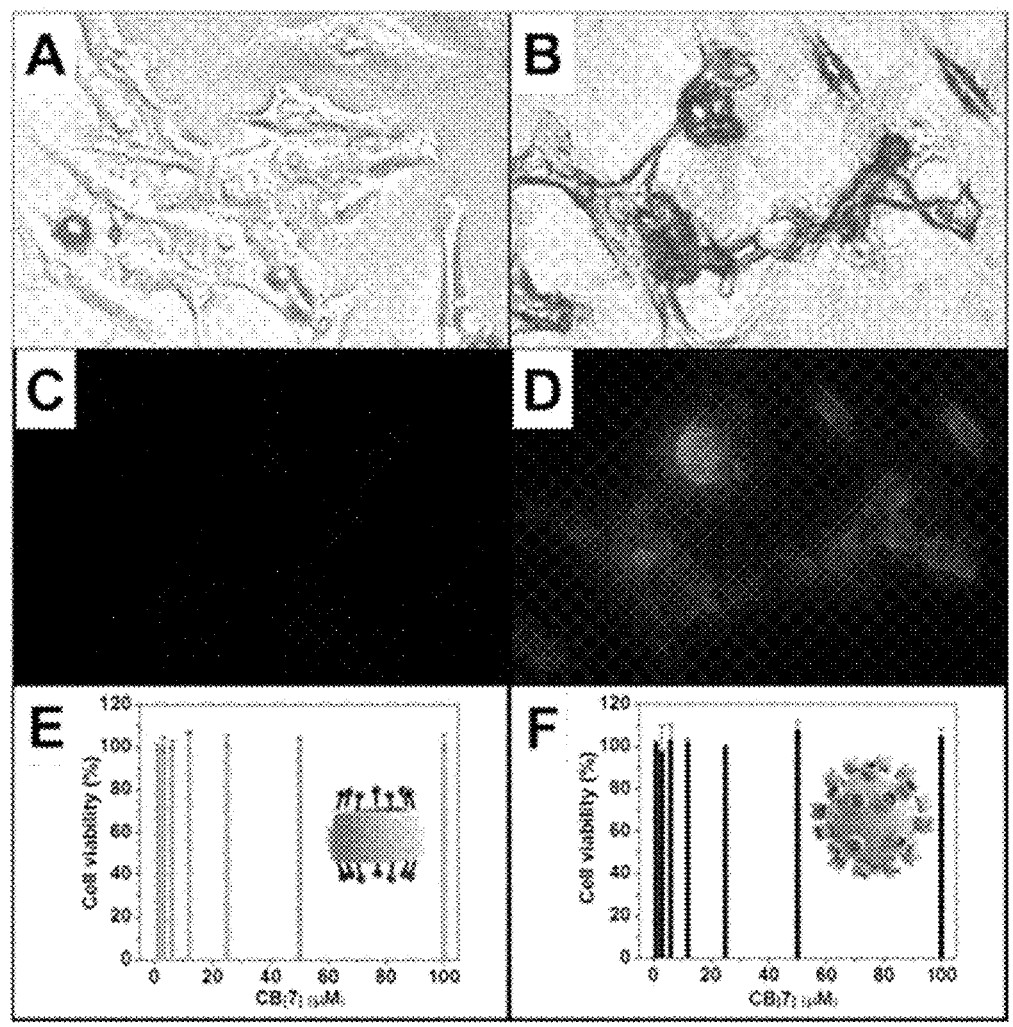
FIG. 11. Optical (A, B) and fluorescence (C, D) microscopy images of HCT116 cells, and plots of % cell viability for samples treated with CB[7] (E) or CB[7]NPs (F). Treated cells (B, D) were incubated with CB[7]NPs ⊃ NR at 5 μM concentration in CB[7] for six hours. Untreated cells (A) show no staining in visible light. After staining, treated cells (B) show a characteristic Prussian blue color which indicates higher intracellular concentrations of iron. Untreated cells (C) emit no red fluorescence, whereas treated cells (D) emit red fluorescence ($\lambda_{max}$=640 nm) characteristic of NR. Neither CB[7] nor CB[7]NPs displayed cytotoxic effects after 24 hours of incubation at concentrations as high as 100 μM.
Figure 20:
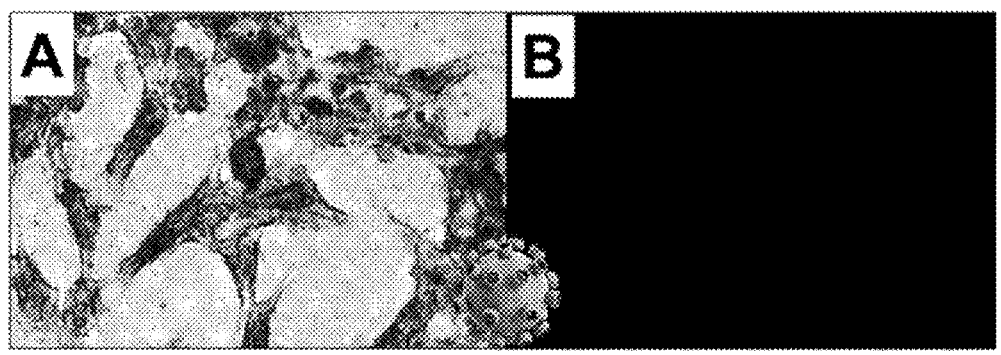
FIG. 20. Optical (A) and fluorescence (B) microscopy images of HCT116 cells treated with CB[7]NPs.

Cell studies. To demonstrate the potential utility of CB[7] NPs as drug delivery vehicles and imaging probes, an in vitro study was carried out using the human colon carcinoma HCT116 cell line and NR as a model hydrophobic drug. The intracellular uptake of CB[7]NPs and CB[7]NPsINR by HCT116 cells was examined by optical and fluorescence microscopies (FIGS. 11 and 20). Iron-containing compounds, including CB[7] NPs, CB[7]NPs ⊃ NR and endogenous iron complexes, give rise to a Prussian blue coloration after staining with potassium ferrocyanide/HCl. As shown in FIGS. 11A and B, optical microscopy confirmed the presence of nanoparticles inside the treated cells. Fluorescence microscopy also confirmed the internalization of CB[7] NPs ⊃ NR as shown in FIGS. 11C and D, with only treated cells (FIG. 11D) displaying the red fluorescence characteristic of the dye in a hydrophobic environment. The strong optical and fluorescence signals in the treated cells and the lack of signals in the untreated cells demonstrate the ability of CB[7]NPs to deliver a drug-like payload.

The cytotoxicy of CB[7] and CB[7]NPs toward HCT116 cells was measured at several different particle-to-cell concentration ratios using the CellTiter-Blue Cell Viability assay (Promega). FIGS. 11E and F show that neither CB[7] nor CB[7]NPs elicit cytotoxic effects on HCT116 cells at CB[7] concentrations of 1 to 100 mM and after 24 hour incubation. These in vitro results constitute a demonstration of biocompatibility.

The CB[7]-functionalized magnetic nanoparticles, CB[7] NPs, can be used for small molecule delivery and in vivo imaging. Microwave heating greatly accelerates the binding of CB[7] to the nanoparticles, and, once formed, the CB[7] NPs are stable in aqueous solutions of pH 2 to 12. The strong interaction between CB[7] and NPs is likely the result of the cooperative binding of seven of the macrocycle's carbonyl groups to the surface of NPs. Direct contact between carbonyl oxygens and $Fe^{3+}$ ions on the surface of the nanoparticles is supported by computational modeling of the interactions between CB[7] and two iron complexes. The presence of CB[7] on NPs provides the intended carrier functionality as well as the added benefit of increased transverse relaxivity, $R_2$. The loading of the CB[7]NPs with NR was confirmed by IR absorbance and fluorescence emission spectroscopies. Release of NR was promoted by the addition of sodium ions which competitively bind to CB[7] and displace NR. The CB[7]NPs were used successfully to deliver NR into HCT116 cells as confirmed by optical and fluorescence microscopies, and they showed no obvious signs of cytotoxicity. The presence of CB[7] on the surface of NPs provides a reversible encapsulation-release process for NR. Bare NPs, however, do not. When incubated with NPs in water for 24 hours, NR was found to bind to the surface of the NPs, as confirmed by both FTIR and fluorescence measurements. However unlike CB[7]NPs ⊃ NR, which release NR in the presence of sodium ions, NPs ⊃ NR do not release NR, as indicated by a lack of fluorescence quenching after addition of sodium. Nevertheless, NR can be efficiently removed from unfunctionalized NPs by organic solvents.

These results indicate that the present compositions can be used involving drug molecules as payloads, alternative release mechanisms, and the contrast enhancement of MR images of live specimens, and as theranostic agents.

General Methods. All reagents were purchased from commercial suppliers (Sigma-Aldrich) and used without further purification. Nanopure water (conductivity of 0.06 μS cm$^{-1}$), obtained from a Millipore Gradiant Elix-3/A10 system was used to prepare the sample solutions. Iron concentration was deduced from ultraviolet-visible absorption spectra recorded with an Agilent Technologies Cary 5000 Series UV-Vis-NIR Spectrophotometer in water at room temperature (298 K). Solutions were examined in 1 cm spectrofluorimetric quartz cells. The experimental error of the wavelength values was estimated to be ±1 nm. Infrared spectra were recorded on an Agilent Technologies Cary 600 Series FTIR Spectrometer using the ATR mode. Size and morphology of the nanoparticles were determined by Transmission Electron Microscopy (TEM, PHILIPS CM20 microscope operating at 200 kV). The powder X-ray diffraction (PXRD) patterns of the samples were collected using a X-ray Panalytical Empyrean diffractometer. The particle size and peak positions were obtained from X-Ray diffraction patterns with HighScore Plus 3.0.5. Hydrodynamic size and ζ-potential measurements were performed on a Malvern Zetasizer NanoSeries. ζ-potential measurements were made on solutions of pH 2 to 12, using automated titration and sample preparation (MPT-2 Autotitrator, Malvern). Thermogravimetric Analyses were performed on a TA SDT Q600 device. Emission spectra were recorded in water, at room temperature, using an excitation wavelength of 510 nm corresponding to the maximum of absorption of the dye (Nile red, NR) using a Perkin Elmer LS55 Fluorescence Spectrometer. Magnetic properties of the nanoparticles were studied using a MIAtek Reader® (Magnetic Immunoassays Technology). The transverse nuclear relaxation times, $T_2$ were measured from axial $T_2$-weighted spin-echo (SE) images obtained with a time repetition (TR) of 2,000 ms and increasing time echo (TEs) of 20, 40, 60, and 80 ms with a 1.5 T MRI scanner (Philips intera 1.5T/ Philips healthcare) at room temperature for various iron concentrations. Optical and fluorescence images were observed on a LEICA DMI 3000B confocal scanning microscope.

Synthesis, characterization and functionalization of $\gamma$-$Fe_2O_3$ nanoparticles (NPs). 1.1. NP synthesis. NPs (8±1 nm) were synthesized by using a previously reported literature procedure.[1,2] A 40% v/v solution of dimethylamine in water (9.0 mL) was added to an aqueous micellar solution (69.5 mL) of ferrous dodecyl sulfate (1.0 mmol). The mixture was stirred vigorously for 2 hours at 28° C. The resulting precipitate was isolated from the supernatant at pH=6.7 (which corresponds to the isoelectric point of the uncoated nanoparticles, NPs) by magnetic separation and washed with $H_2O$. Formation of the NPs was confirmed by TEM.

Surface functionalization of NPs with CB[7]. A) Conventional heating. An aqueous solution (1 mL) of CB[7] (n=3×$10^{-5}$ mol) was added to the colloidal suspension (4 mL, $n_{Fe}$=7×$10^{-4}$ mol) of NPs (NPs:CB[7]=1:1000 ratio) and the mixture was stirred for 24 hours at room temperature. NPs were precipitated using a magnet and washed with water repeatedly without centrifugation to remove excess of CB[7].

The same functionalization procedure was also conducted at 50° C. in order to determine the effect of temperature. In both cases, iron concentration was deduced from UV-Vis spectroscopy measurements.

B) Microwave heating. An aqueous solution (1 mL) of CB[7] (n=3×$10^{-5}$ mol) was added to the colloidal suspension (4 mL, $n_{Fe}$=7×$10^{-4}$ mol) and the mixture was transferred to a 10 ml, vessel with a crimp cap and heated by microwave irradiation of 2.45 GHz in a microwave reactor (CEM Discovery, CEM Inc. USA). The power was modulated in order to reach a temperature of 50° C. in one minute and to maintain that temperature for 30 minutes. The maximum power applied was 300 W. Stirring was initiated at 50° C. during the heating cycle. One or two heating cycles were used to prepare CB[7]NPs, with two cycles being optimal. The NPs were washed with water and precipitated by using a magnet. Iron concentration was deduced from UV/Vis absorption data.

Encapsulation of Nile Red (NR) by CB[7] on CB[7]NPs. CB[7]NPs ($n_{CB[7]}$=6×$10^{-4}$ mol) and NR (6×$10^{-4}$ mol) were mixed in water (2 ml) and stirred for two hours at room temperature to form inclusion complexes on the surface of NPs. The product was precipitated by using a magnet and washed several times with water; the brown solid was designated CB[7]NPs⊃NR. The encapsulation of NR was confirmed by FTIR, fluorescence emission spectrometry and ζ-potential measurements.

NP Characterization. Fourier Transform Infrared (FTIR) Spectroscopy. Surface coating of NPs was confirmed and characterized an Agilent Technologies Cary 600 Series FTIR Spectrometer. FIG. 13 shows the FTIR spectra of A) CB[7] B) uncoated $\gamma$-$Fe_2O_3$ nanoparticles, NPs C) CB[7]NPs synthesized at room temperature (24 hours) D) CB[7]NPs synthesized by conventional heating at 50° C. (24 hours) E) CB[7]NPs synthesized by microwave heating at 50° C. for 30 minutes F) CB[7]NPs synthesized by microwave heating at 50° C. for 2×30 minutes and G) CB[7]NPs⊃NR.

The NPs synthesized by two cycles of microwave heating at 50° C. for 30 minutes were used exclusively for all subsequent studies involving adsorption of CB[7] and encapsulation of NR.

FIGS. 12A and 12B show the FTIR absorption spectra of CB[7] molecules and NPs. CB[7] is symmetrical, with two identical carbonylated portals that give rise to a single C—O stretching vibration at 1723 $cm^{-1}$. Additional absorption bands that correspond to C—H, N—H and C—C vibrations in CB[7] are also present in the spectrum. Contact with NPs desymmetrizes CB[7] and gives rise to two distinct C=O absorption peaks at 1734 and 1633 $cm^{-1}$ which are apparent in FIGS. 12(C-F). FIG. 12G shows a spectrum of CB[7]NPs (obtained from microwave heat at 50° C. for 2 cycles of 30 minutes) after complexation with NR. The similarity of this spectrum to that shown in FIG. 13 indicates that CB[7] remains on the surface of the NPs after host-guest complexation.

FIG. 13 displays the FTIR spectra of CB[7]NPs at pH 3, 7 and 12. These results clearly showed the presence of complexed CB[7] on the NPs surface all over the pH range.

Figure 14:
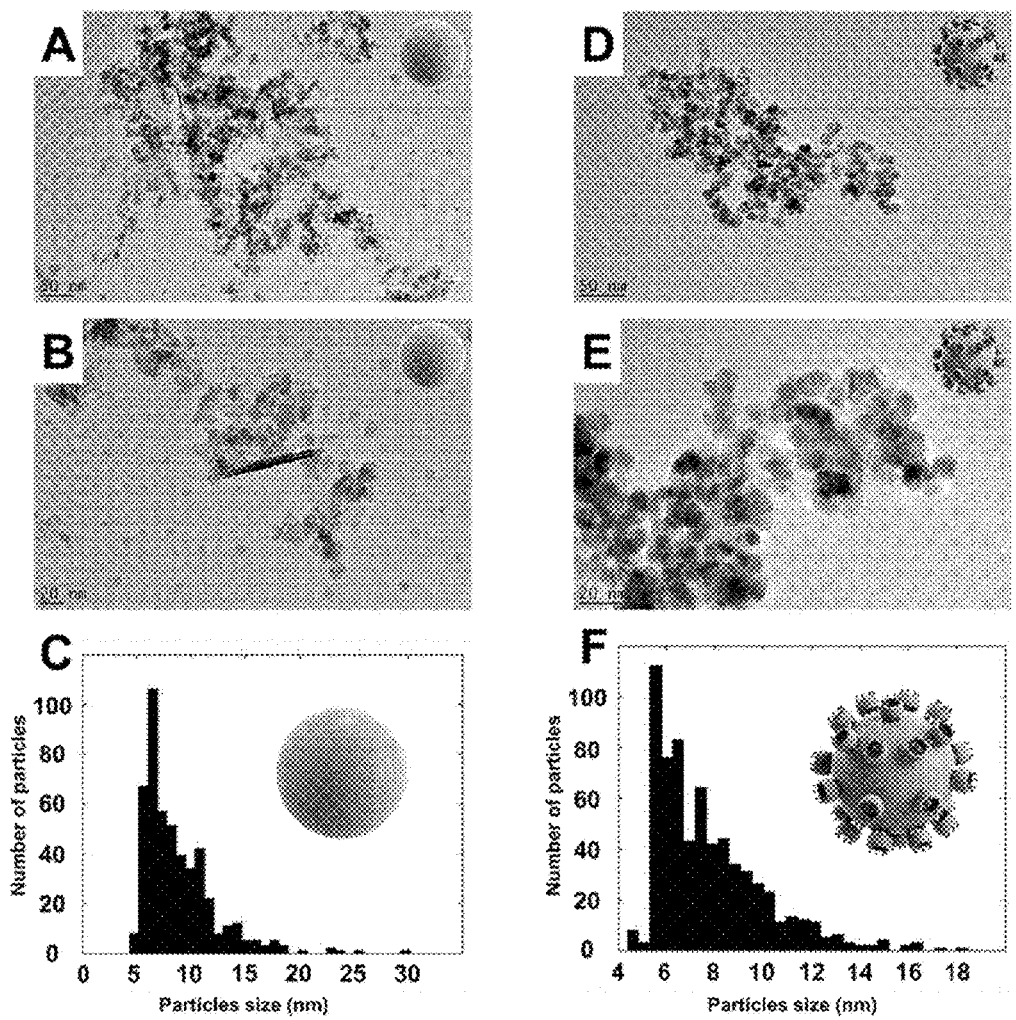
FIG. 14. HRTEM images of NPs (A, B), and CB[7]NPs (D, E). Histograms show the particles size distribution of NPs (C) and CB[7]NPs (F).

Transmission Electron Microscopy (TEM). Size and morphology of the nanoparticles were determined with a PHILIPS CM20 microscope operating at 200 kV. Samples were prepared on a carbon-coated copper grid. A drop of NP solution ([Fe]=1.0×$10^{-5}$ M) was spotted on the grid and allowed to dry overnight. FIG. 14 shows NPs before (A, B) and after (D, E) surface functionalization with CB[7]. The particle size distribution was determined using a standard methodology. In both cases the nanoparticles are 8±1 nm in diameter (mean diameter) and present a spherical shape.

Figure 15:
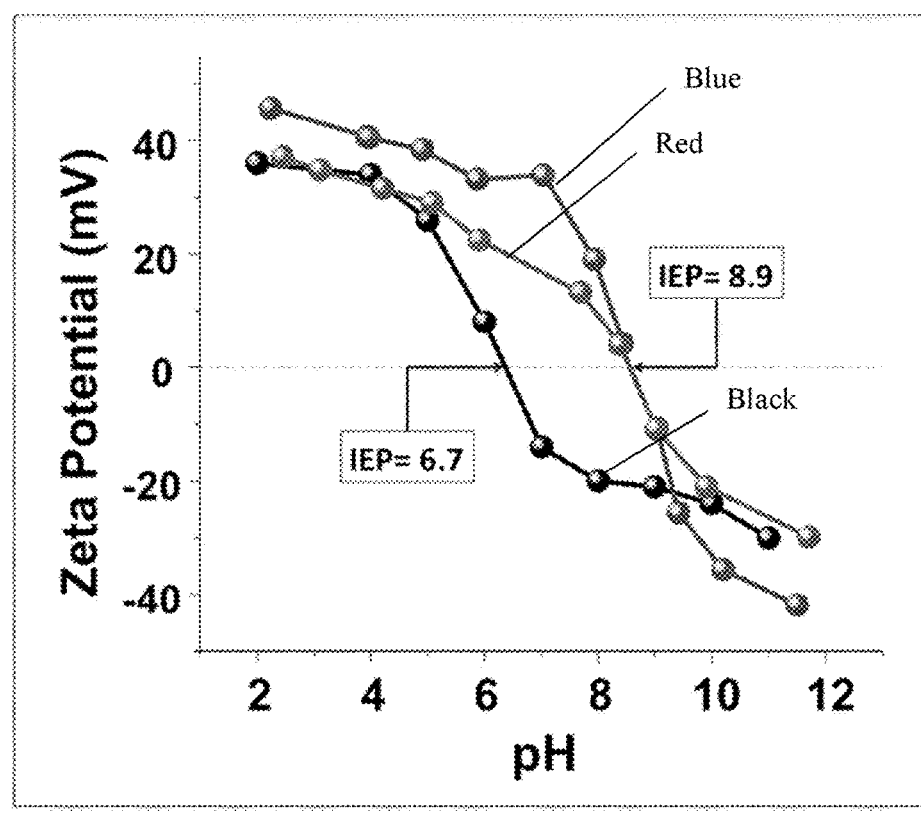
FIG. 15. ζ-potential measurements as function of the pH of NPs (black curve), CB[7]NPs (blue curve) and CB[7] NPs ⊃ NR (red curve).

Dynamic Light Scattering (DLS) Characterization. DLS measurements were carried out on a Zetasizer Nano-ZS (Malvern Instruments) to determine hydrodynamic size and ζ-potential. All samples were analyzed at room temperature in water with diluted ferrofluid ([Fe]=1×$10^{-3}$ M). FIG. 15 illustrates the ζ-potential measurements performed at pH=2 to 12 using automated titration and sample preparation (MPT-2 Autotitrator, Malvern).

Thermogravimetric Analysis (TGA). The weight percentage (Table 1) of CB[7] on the surface of CB[7]NPs was determined by TGA. Solid samples (10 mg) under $N_2$(g) flux were characterized with a SDT Q600 TA Instruments analyzer at a heating rate of 5° C./min over a temperature range of 35-700° C. FIG. 16 shows the weight losses of the $\gamma$-$Fe_2O_3$ NPs, and CB[7]NPs. The TGA analysis of CB[7] NPs shows a composition of 94.84% iron oxide and 4.33% of CB[7]. With the following equation, these percentages can be used to calculate the number of CB[7] macrocycles per NP.

TABLE 1

TGA calculations for NPs and CB[7]NPs nanoparticles.

|  | Weight loss (%) | Mass in 1 g (g) | n in 1 g (mol) | Number of entity in 1 g |
|---|---|---|---|---|
| $\gamma$-$Fe_2O_3$ (NPs) | 94.84 | $m_{Fe_2O_3}$ = 0.95 | $n_{Fe}$ = 12 × $10^{-3}$ | *$N_{nano}$ = 1.7 × $10^{18}$ |
| CB[7] | 4.33 | 0.04 | 4.0 × $10^{-5}$ | 2.5 × $10^{19}$ |

$$N_{nano} = \frac{n_{Fe2O3} \times M_{Fe2O3}}{\rho \times \frac{4}{3} \times \pi \times R^3}$$

(*) Where R is the radius of NP, as obtained from TEM analysis, ρ is their density, $M_{NPs}$ is the molar mass of γ-$Fe_2O_3$, and $n_{NPs}$ is the number of moles of NPs as deduced from TGA analysis.[4] An average number of 27 CB[7] molecules per nanoparticle can be calculated. This result is in reasonable agreement with theory which predicts that the surface of an NP that has a diameter of 8 nm would be able to. If we consider the surface of a nanoparticle with a diameter of 8 nm (surface area=200.96 $nm^2$) would be able to accommodate a maximum of 25 molecules of CB[7]. We therefore conclude that the density of the nanoparticle coverage is nearly 100%.

FIG. 16 presents the weight losses of CB[7]NPs before (red curve) and after (black curve) encapsulation of the NR dye. An additional weight loss that corresponds to NR can be observed and is consistent with an equimolar complexation of NR with CB[7]. These data clearly testify to the successful encapsulation of NR into the cavities of the CB[7] macrocycles.

Figure 17:
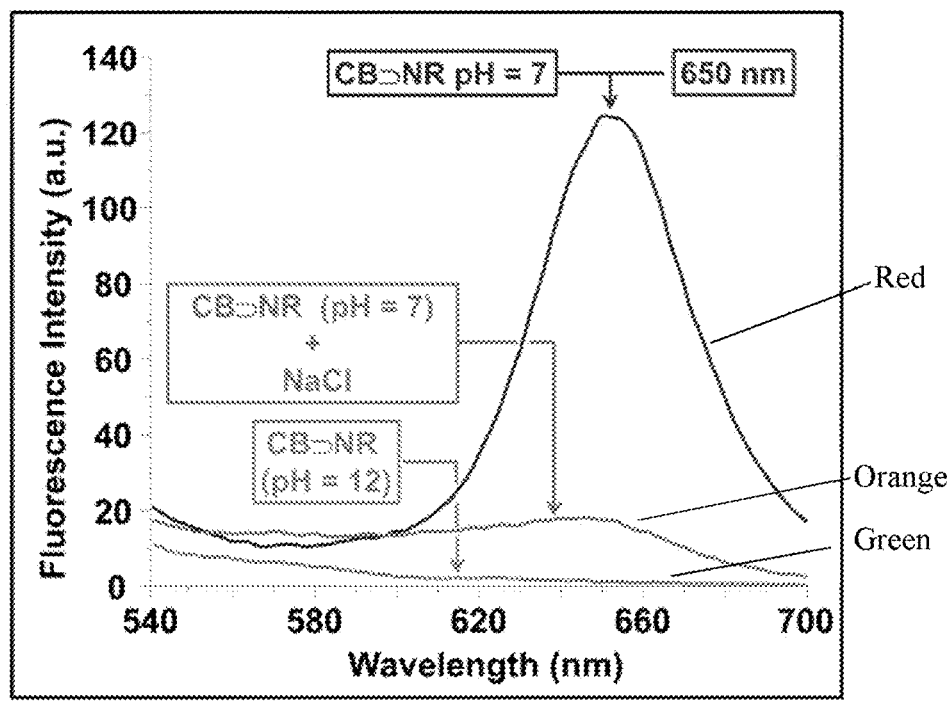
FIG. 17. Fluorescence emission spectra of CB[7] ⊃ NR at pH=7 (red curve), CB[7] ⊃ NR at pH=12 (green curve), CB[7] ⊃ NR at pH=7 in presence of NaCl (orange curve), (Solvent: H$_2$O, room temperature, λex=510 nm)

Fluorescence emission spectroscopy. Fluorescence from CB[7]NPs⊃NR nanoparticles was measured by a Perkin Elmer LS55 Fluorescence Spectrometer using 510 nm as the excitation wavelength (maximum of absorption of NR). It is known that NR does not fluoresce in water (FIG. 17) but emits red fluorescence in a hydrophobic environment. Fluorescence measurements showed characteristic emission ($\lambda_{max}$=650 nm) of NR in water at pH 7 upon encapsulation with CB[7] (CB[7]⊃NR, FIG. 17). By adjusting the pH to 12, the added sodium ions ([$Na^+$]=$10^{-2}$ M) compete with NR for the carbonyl portal of CB[7] and consequently diminish the NR fluorescence signal. This result is confirmed by the addition of NaCl, which causes a similar decrease of the fluorescence intensity over time.

In serum: An aqueous solution (100 μL) of CB[7]NPs⊃NR ([Fe]=$1.6\times10^{-1}$ M, $n_{Fe}$=$1.6\times10^{-5}$ mol, nCB[7]=$2\times10^{-8}$ mol) was added to 3 mL of Fetal Bovine Serum (FBS). The mixture was stirred for twenty-four hours at room temperature. The product was then precipitated by centrifugation and washed with water.

For fluorescence measurements recorded in water, the solution was diluted 3 times and compared to those that were measured at the same concentration but had not been incubated in serum. Fluorescence measurements show no significant decrease of emission intensity of NR, an indication that NR remains in the cavity of CB[7]. The hydrodynamic diameter of CB[7]NPs⊃NR in pure serum was measured and found to be d=25.17 nm (IDPs=0.33). d=24.21 nm after washing with water.

Figure 18:
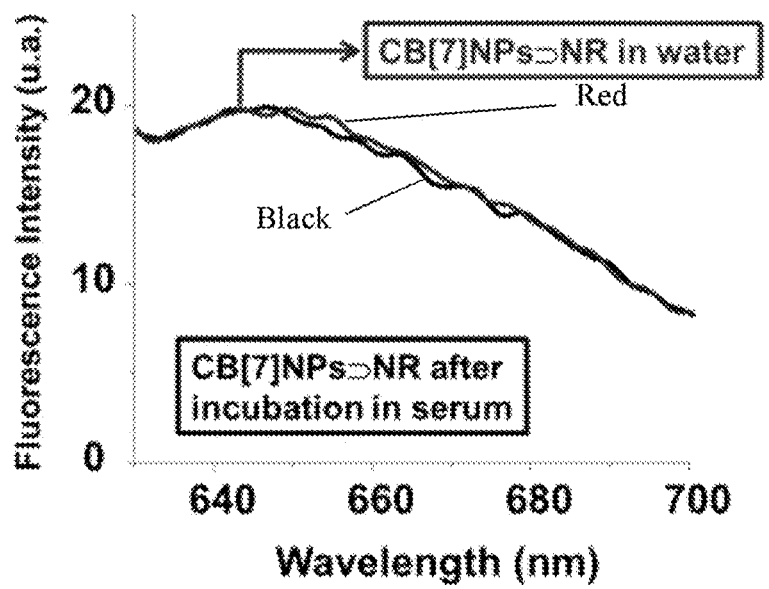
FIG. 18. Comparison of the emission spectra of CB[7] NPs-NR before (red) and after (black) incubation in FBS for 24 hours at room temperature. Both spectra were recorded in water at room temperature using λex=510 nm.

FIG. 18: comparison of the emission spectra of CB[7]NPs-NR before (red) and after (black) incubation in FBS for 24 hours at room temperature. Both spectra were recorded in water at room temperature using λex=510 nm.

TABLE 2

Hydrodynamic size and zeta potential values of CB[7]NPs⊃NR in pure FBS after 24 hours, and in water after the removal of FBS

|  | Hydrodynamic Size d (nm) | Zeta-potential (ζ) |
|---|---|---|
| CB[7]NPs⊃NR in FBS | 25.17 | −6.4 |

TABLE 2-continued

Hydrodynamic size and zeta potential values of CB[7]NPs⊃NR in pure FBS after 24 hours, and in water after the removal of FBS

|  | Hydrodynamic Size d (nm) | Zeta-potential (ζ) |
|---|---|---|
| CB[7]NPs⊃NR in H2O (after removing FBS) | 24.17 | −3.6 |

Magnetic properties study (MIAtek®). Magnetic properties of the nanoparticles, NPs and CB[7]NPs⊃NR, were studied using a MIAtek® reader (Magnetic Immunoassays Technology), which measures a signal proportional to the third derivative of magnetization at zero magnetic field. The detection method was based on the nonlinear magnetization of superparamagnetic iron oxide nanoparticles. An alternating magnetic field was applied to the sample at two different frequencies $f_1$=100 kHz and $f_2$=100 Hz having amplitudes of 10 and 200 Oe, respectively. The response of the sample was measured at combinatorial frequencies, e.g., $f=f_1\pm2\times f_2$.[6] Compared to NPs, CB[7]NPs and CB[7]NPs⊃NR are less aggregated as a consequence of having more positive charge on their surface. This difference explains the increase of the Miatek® Signal assembled in Table 3.

TABLE 3

MIAtek® signal of NPs, CB[7]NPs, and CB[7]NPs⊃NR.

|  | NPs | CB[7]NPs | CB[7]NPs⊃NR |
|---|---|---|---|
| Miatek Signal (a.u./mg) | 189,253 | 444,846 | 551,225 |

MRI Contrast Agent Evaluation. The $^1$H NMR relaxometric characterization was performed by measuring the transverse nuclear relaxation times $T_2$, on a 1.5 T MRI scanner. The measurements were performed at room temperature for various iron concentrations between 0.07 and 0.25 mM. $T_2$ maps were calculated assuming a monoexponential signal decay and accordingly from four SE images with a fixed TR of 2,000 ms and TE values of 20, 40, 60, and 80 ms. The signal intensity for each pixel as a function of time was expressed as follows: SIpixel xy(t)=So(pixel xy)exp(-t/$T_2$pixel xy). $T_2$ relaxation times were then deduced by ROI measurements using Image J software. The efficiency of MRI contrast agent was determined by measuring the relaxivities $R_2$ defined as $R_2$=[$(1/T_2)_{meas}$−$(1/T_2)_{dia}$]/C, where $(1/T_2)_{meas}$ is the value measured with the sample at concentration C of iron, and $(1/T_2)_{dia}$ refers to the nuclear relaxation rate of the diamagnetic host solution (water in our case). The signal intensity of $T_2$ weighted images changed substantially with an increasing amount of nanoparticles (FIG. 19A), indicating that the nanoparticles generated MR contrast on transverse ($T_2$) proton relaxation times weighted sequences. FIG. 19B shows the relaxation rate 1/$T_2$ as a function of the iron concentration. As expected, the relaxation rates varied linearly with the iron concentration. The transverse $R_2$ relaxivities (corresponding to the slopes of the lines) for the CB[7]NPs and CB[7]NPs⊃NR nanoparticles are shown in FIG. 19B.

Cell lines and culture. HCT116 human colon carcinoma cells were obtained from the American Tissue-Type Culture Collections (ATCC). The cell line was grown in McCoy's 5A medium supplemented with 10% fetal bovine serum (FBS), at 37° C. in a 5% $CO_2$ humidified incubator.

In vitro studies cellular uptake: The intracellular uptake of CB[7]NPs (FIG. 20) and CB[7]NPs⊃NR was examined using fluorescence microscopy and Prussian blue staining (CB[7] and NR concentrations=5 μM) using HCT116 cells. HCT116 cells were seeded in Petri dishes (⌊ 30 mm, density $2\times10^5$ cells per Petri dish), grown for 24 hours and treated for 6 hours with CB[7]NPs and CB[7]NPs⊃NR nanoparticles. The cells were then washed three times with PBS, fixed with paraformaldehyde (10 min) and dried at room temperature. The attached cell monolayer was incubated with 5% potassium ferrocyanide (5 min), washed with PBS and then incubated again with a solution containing 5% potassium ferrocyanide and 10% hydrochloric acid for 10 min and washed with PBS three times. Staining (bright blue pigment) results from the reaction between the $Fe^{3+}$ ions present in the nanoparticles and the ferrocyanide ions. The iron particles in the cells were observed as blue dots using an optical microscope with phase contrast. The experiment was performed in triplicate.

In vitro cytotoxicity assay. Cell viability was evaluated using the Promega CellTiter-Blue® Cell Viability assay. It uses the indicator dye resazurin to measure the metabolic capacity of cells—an indicator of cell viability. Viable cells retain the ability to reduce resazurin into resorufin, which is highly fluorescent. Nonviable cells rapidly lose metabolic capacity, do not reduce the indicator dye, and thus do not generate a fluorescent signal. HCT116 cells were seeded at a density of $5\times10^4$ cells per well in 96-well flat-bottom plates and incubated in 10% FBS-medium for 24 hours. Then, medium was removed and replaced by 10% FBS-medium containing free CB[7] and CB[7]NPs with increasing CB[7] concentrations from 100 μM to 1 μM. After 24 hours incubation, cells were washed with phosphate buffered saline (PBS, Amresco Biotechnolgy grade) and incubated with 20 μL of CellTiter-Blue® Reagent for additional 6 hours at 37° C. The fluorescence corresponding to the resorufin (which reflects the relative viable cell number) was measured at 590 nm using a Synergy H1 Hybrid Reader Biotek. The measurement was performed on untreated cells as a blank control.

Computational Details. All calculations presented in this work were performed employing the Gaussian 09 package (Revision B.01). Full geometry optimizations of the 1, $(1)_2$ . . . $OH_2$, 1 . . . $(H_2O)Fe(OH)_3$ and $1\text{-Fe(OH)}_3$ systems were performed employing DFT within the hybrid meta-GGA approximation with the TPSSh exchange-correlation functional. In these calculations we used the standard Ahlrichs' valence triple-ζ basis set including polarization functions (TZVP). No symmetry constraints have been imposed during the optimizations. The stationary points found on the potential energy surfaces as a result of geometry optimizations were tested to represent energy minima rather than saddle points via frequency analysis. The default values for the integration grid (75 radial shells and 302 angular points) and the SCF energy convergence criteria ($10^{-8}$) were used in all calculations. The two systems containing Fe(III) were modeled in their high-spin configurations (S=5/2) using an unrestricted model. Thus, spin contamination was assessed by comparison of the expected difference between S(S+1) for the assigned spin state (S=5/2) and the actual value of $\langle S^2 \rangle$. The results indicate that spin contamination is negligible ($\langle S^2 \rangle - S(S+1) < 0.0071$) in both cases.

The IR absorption profiles were calculated by the formula:

$$A(E) = \sum_i \frac{2.174\times 10^9 I_i}{\Delta_{1/2}} \exp(-2773(E-E_i)^2/\Delta_{1/2}^2)$$

where the sum runs over all calculated IR frequencies with energies $E_i$ (in $cm^{-1}$) and IR intensities $I_i$, obtained using analytical second derivatives, and $\Delta_{1/2}$ represents the half-bandwidths. Thus, the total integrated intensity under the absorption profile equals the sum of the IR intensities, $$\sum_i I_i.$$

Simulated spectra were obtained using $\Delta_{1/2}$ values of 30 $cm^{-1}$ for all bands, except those corresponding to the carbonyl stretching vibrations, for which $\Delta_{1/2}$ was set to 50 $cm^{-1}$. A scaling factor of 0.97 was applied to improve the agreement between theoretical and calculated spectra.

Example 2

Figure 24:
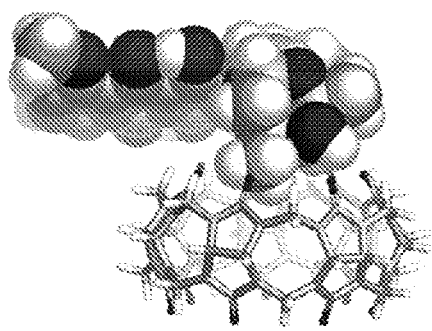
FIG. 24. A) Representation of energy-minimized structure of doxorubicin and CB[7]. B)$^1$H NMR resonances of Dox as a function of increasing the concentration of CB[7] are shown.
Figure 24:
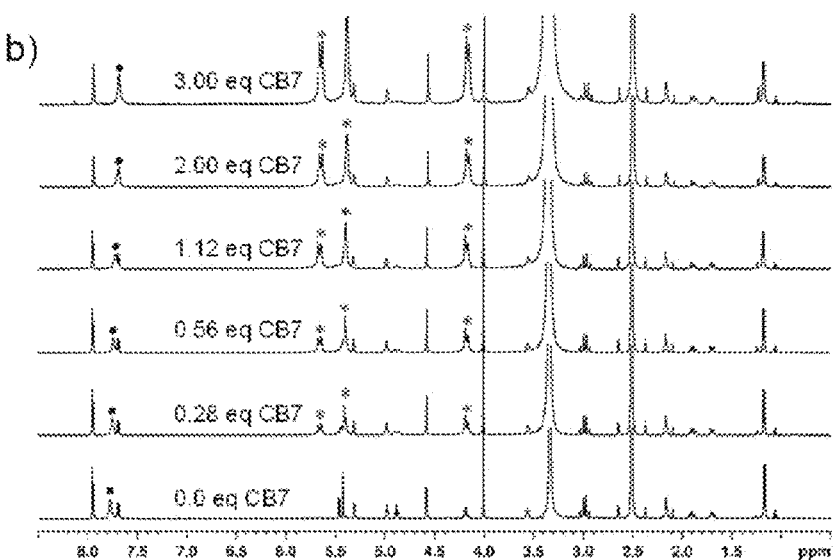

The interaction between Dox and CB[7] was initially evaluated computationally using density functional theory (DFT) calculations. (CARLOS) The calculations gave an insight on the mode of interaction, when the structure with the lowest energy level was obtained. The energy minimized structure presented in FIG. 24a) illustrates that there is an interaction between the hydroxyl and ammonium groups on the sugar ring in the drug with the carbonyl groups on the rim of the CB[7]. The interaction of Dox with macrocycle was then investigated in solution through a qualitative $^1H$ NMR titration experiment of a DMSO solution of Dox with increasing amounts of CB[7]. The gradual shift in some of the $^1H$ NMR resonances of Dox as a function of increasing the concentration of CB[7] are demonstrated in FIG. 24b. Spectral shifts highlighted by the major upfield shift of the protons of the ammonium group (7.75 ppm in the absence of CB[7] to 7.69 ppm in the presence of 3.00 eq of CB[7]) on the sugar ring of the drug matches the modeled mode of interaction of the complex. We inferred from these initial results that a similar binding would occur between Dox and CB[7] macrocycles adsorbed on the surface of NPs.

TGA measurements reveal that an average of 1:1 CB[7]-Dox is present on the surface of the NPs. In addition, as revealed by DLS studies, addition of Dox changed the overall charge of the nanoparticles. The isoelectric point shifts from pH 8.9 for CB[7]NPs to pH 5.0 upon DOX encapsulation. This surface modification is an evidence of successful loading of DOX into CB[7]NPs. Moreover, at pH 7.4, ζ-potential of CB[7]NPs moves from +35 mV to −20 mV when DOX is encapsulated on the nanoparticle surface. This change in surface charge causes enough repulsion between Dox-CB[7]NPs to maintain them stable at physiological pH minimizing aggregation of the particles.

The pH, glutathione, or heat-triggered Dox release was monitored using fluorescence spectroscopy. After fully characterizing the Dox-CB[7]NPs complex in solution and establishing the presence of Dox within CB[7]NPs, the triple-activated release of Dox in solution was carried out. Initially at pH 7.4, room temperature and in the absence of glutathione, the emission of the Dox was observed to be quenched as a result of its proximity to the nanoparticles. After applying the stimulus, release of the Dox from CB[7] NPs was observed by exciting the solution with a λex=488 nm which corresponds to the maximum of Dox absorption. Release % of Dox was observed as a function of time for the pH and glutathione stimuli and as function of temperature for the heat stimulus.

Figure 25:
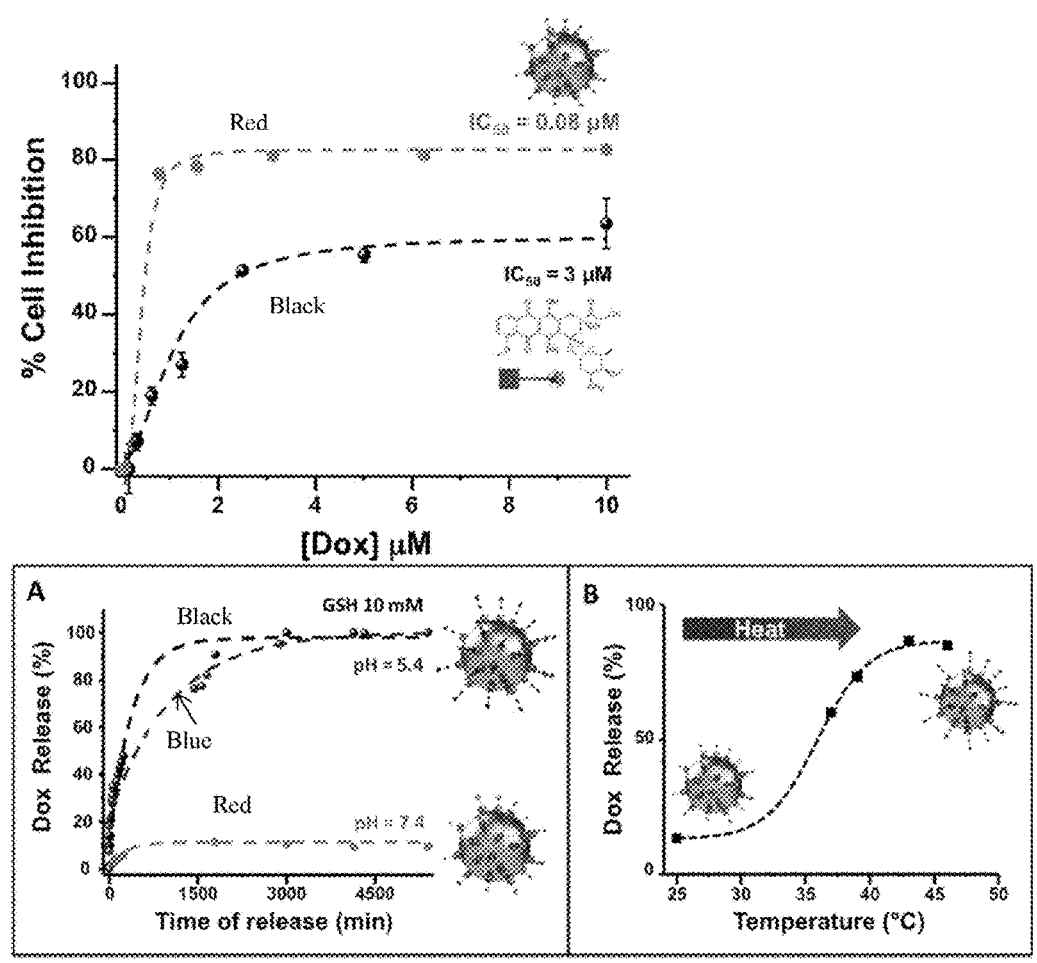
FIG. 25. A) In vitro Dox release profiles for Dox-CB[7] NPs at pH 7.4 without (red curve) and with (black curve) 10 mM glutathione (GSH) and at pH 5.4 (blue curve). B) In vitro release of Dox from Dox-CB[7]NPs from aqueous solution at pH 7.4 as a function of temperature.

The pH-induced Dox release profiles were monitored after adjusting the pH of the solution of Dox-CB[7]NPs to the desired value using HCl or NaOH (1M). At pH 7.4 and at room temperature, the release profile of Dox (FIG. 25) revealed insignificant premature release (10% over 4 days) of the drug as indicated by the low emission intensity increase, during the course of the experiment which demonstrates that the Dox-CB[7]NPs are stable at physiological pH and room temperature. Upon acidifying the solution to 5.4, an enhancement of the Dox emission was observed, which indicates the release and diffusion of Dox in solution. 95% of the Dox was released over 2 days at pH 5.4. This observation can be attributed to the competitive binding of hydronium ions ($H_3O^+$) to the cavity of CB[7] which trigger the dissociation of the Dox into the solution. Interestingly, under acidic pH, CB[7]NPs slowly delivered the drug over 5 days which could be interestingly for a longer duration of action of drug if the NPs vehicle can be kept at the same site.

The glutathione-responsive release profile of the Dox-CB[7]NPs indicates that the glutathione interacts with the surface adsorbed CB[7] macrocycles, as demonstrated by solution $^1H$ NMR experiments and DFT calculations. GSH trigger the release of the Dox into the solution as confirmed by the increase of the emission intensity in presence of GSH measured by fluorescence We believe that Dox release from Dox-CB[7]NPs is the result of competition between Dox and GSH for the CB[7] cavity. This hypothesis was investigated by evaluating the interaction of the GSH and CB[7] computationally and experimentally. The interaction was modelled computationally through DFT studies. In solution, a $^1H$ NMR titration of CB[7] solution to a solution of GSH in $D_2O$ was performed. The gradual spectral shifts of the glutathione proton NMR signals upon increasing the concentration of CB[7] are consistent with an interaction between the two species in solution.

The glutathione-triggered release of Dox from Dox-CB[7]NPs is slightly faster compared to the acidic stimulus with approximately 50% of the drug being released after 4 hours while 9 hours are needed in the case of acid triggered release. However a prolonged release over 4-5 days can still be observed which shows that the glutathione-triggered release is competitive with the pH-induced release.

With the chemically induced (pH and glutathione) release mechanism of the Dox understood, Dox-loaded CB[7]NPs were subjected to heat in order to observe the effect of temperature on the release of drug and in view of hyperthermia application. The heat-induced release profile of Dox indicates that the Dox-CB[7]NPs are stable at physiological pH and at room temperature. An increase in the solution temperature gradually to 45° C. triggers the release of the Dox in solution as demonstrated by the increase of the emission intensity of the Dox.

The heat-responsive character of CB[7]NPs coupled to its chemotherapeutic properties represent a strategy for achieving a combined therapy which maximizes the chance of successful treatment and eliminate tumors. In view of these results, Dox-CB[7]NPs were subjected to an external magnetic field (AMF) and in order to evaluate the magnetic induced release of Dox and their heat-mediating properties.

Nanoparticles that exhibit high magnetization are potentially suitable for a range of applications including MRI, hyperthermia treatments, drug delivery, and magnetic separation. The magnetization curves (FIG. 35) for both CB[7] NPs and Dox-CB[7]NPs are characteristic of superparamagnetic nanoparticles and are consistent with maghemite nanoparticles of 10 nm diameter. However, Dox-CB[7]NPs exhibited a significantly greater $M_{sat}$ (45.1 emu·$g^{-1}$) than CB[7]NPs (18.8 emu·$g^{-1}$). The superparamagnetism and high $M_{sat}$ value of Dox-CB[7]NPs make them ideal candidate agents for magnetic fluid hyperthermia treatments and magnetically controlled drug release.

Figure 26:
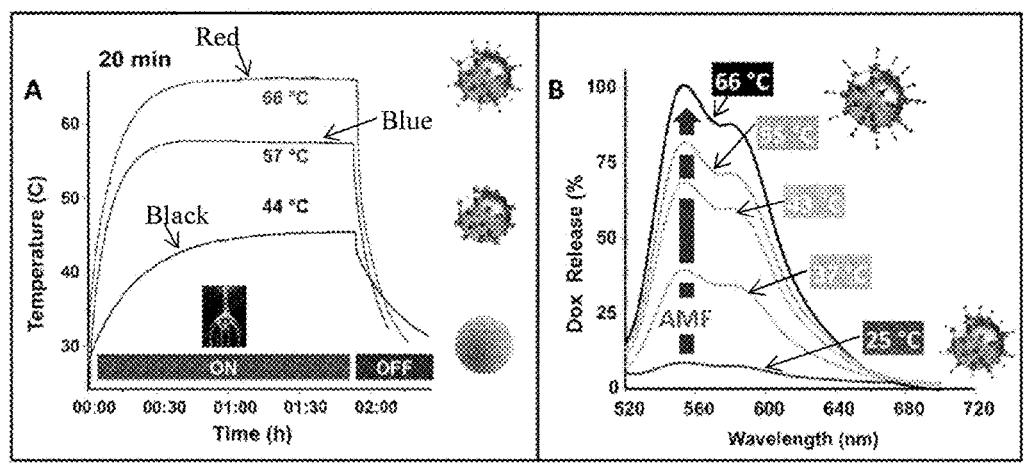
FIG. 26. A) Temperature response curves for solutions of bare NPs (black curve), CB[7]NPs (blue curve) and Dox-CB[7]NPs (red curve) upon application and removal of an oscillating magnetic field ([Fe]=0.2 M, time=2 hours, 464 kHz); B) Fluorescence emission spectra of a solution of Dox-CB[7]NPs (red curve, pH=7, [Fe]=0.05 M, 298 K, λex=488 nm) and after exposure of the solution to an oscillating magnetic field (pH=7, c$_{Fe}$=0.05 M, time=30 minutes, 464 kHz) showing the gradual release of the drug as a function of the temperature rose in the solution.

Solutions of bare NPs, CB[7]NPs and Dox-CB[7]NPs were each placed in an oscillating magnetic field in order to determine the ability of the nanoparticles to heat the solution. Samples at a concentration of 0.2 M iron and room temperature were placed inside a water-cooled copper coil that produced an alternating current (AC) magnetic field (AMF) of 464 kHz frequency and 26.8 k$Am^{-1}$ amplitude (Magnetherm, UK). The temperature of the solutions was monitored and found to increase to a maximum of 44° C. when heating was mediated by bare NPs, and to a maximum of 57° C. and 68° C. when heating was mediated by either CB[7]NPs or Dox-CB[7]NPs (FIG. 26A). When the oscillating magnetic field was removed, the temperature of all solutions decreased to room temperature. Also, during the magnetically induced heating period, the sample of Dox-CB[7]NPs lost 70% and 100% of its drug cargo over 30 minutes as monitored by fluorescence spectroscopy when the temperature reached 42 and 68° C. respectively which demonstrates that Dox-CB[7]NPs can be used as bifunctional agents that combine thermo- and chemotherapeutic modes of action. (FIG. 26B).

Figure 27:
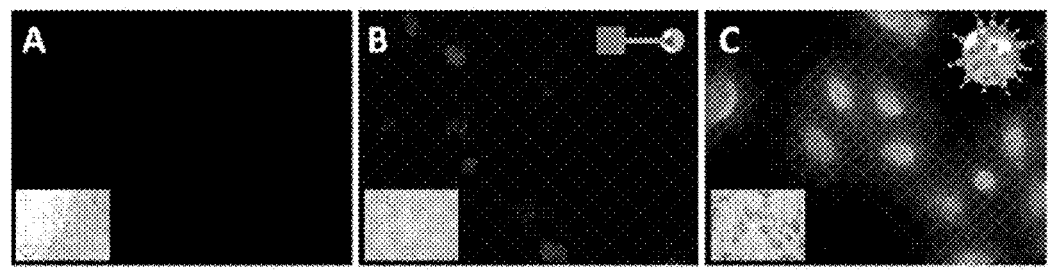
FIG. 27. Fluorescence images of HeLa cells. Untreated cells (A) show no signal in fluorescence mode. Cells treated with Dox (B, 2 hours, [DOX]=10 μM) are weakly fluorescent. Cells treated with Dox-CB[7]NPs (C, 2 hours, [DOX]=10 μM) are strongly fluorescent (inset: Optical images).

After establishing the presence of Dox within the CB[7] NPs delivery vehicle and understanding the release mechanism of Dox from the drug delivery vehicle in solution, Dox-CB[7]NPs were subjected to cellular experiments to study the internalization of the nanoparticles in HeLa cancer cells and evaluate their potential therapeutic character compared to free Dox. The cellular uptake of both free drug (Dox) and drug-loaded NPs was observed using fluorescence microscopy (FIG. 27A-C). Comparison of photomicrographs of HeLa cancer cells incubated with Dox or Dox-CB[7]NPs (same dose of Dox) for 3 hours at 37° C. demonstrate that the CB[7]NPs enhance the cell uptake of Dox since the strong red emission observed with Dox-CB[7]NPs compared to the weak emission observed with Dox. The normalized fluorescence intensity detected with Dox is 40% of the red emission of Dox-CB[7]NPs on excitation at 488 nm.

Figure 28:
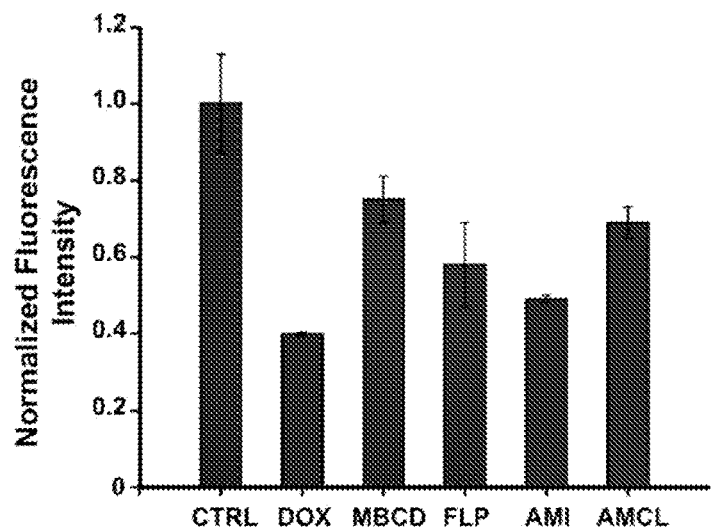
FIG. 28. Effect of endocytotic inhibitors on cellular uptake of Dox-CB[7]NPs into HeLa cells. Left to right, the first two blue bars indicate the normalized fluorescence of cells incubated for 2 hours with Dox-CB[7]NPs (CTRL) or Dox alone (DOX). The other bars indicate the normalized fluorescence of cells incubated for 2 hours with Dox-CB[7] NPs and either methyl-β-cyclodextrin (MBCD), filipin (FLP), amiloride (AMI) or ammonium chloride (AMCl). MBCD, FLP, AMI and AMCL are inhibitors of lipid raft synthesis, caveolin-dependent endocytosis, macropinocytosis and endosome acidification, respectively.

To determine the nature of the active entry mechanisms of Dox-CB[7]NPs and the relative contribution of these mechanisms to cellular uptake, chemical inhibitors of the various endocytic pathways were employed (FIG. 28). By measuring the fluorescence intensity inside the cells, we found that macropinocytosis and caveolin-dependent endocytosis are the primary uptake mechanisms. By inhibiting the lysosome acidification, we also found that Dox is partially released from the NPs in lysosomal compartments, a result consistent with the acidity of the microenvironment (pH 5.0-5.5) of these organelles. The remaining of Dox is most-likely released as a consequence of the relatively high concentrations of GSH within cancer cells. The facile release of Dox into the cytoplasm is highly advantageous and increases the suitability of Dox-CB[7]NPs for targeted intracellular drug delivery.

Figure 29:
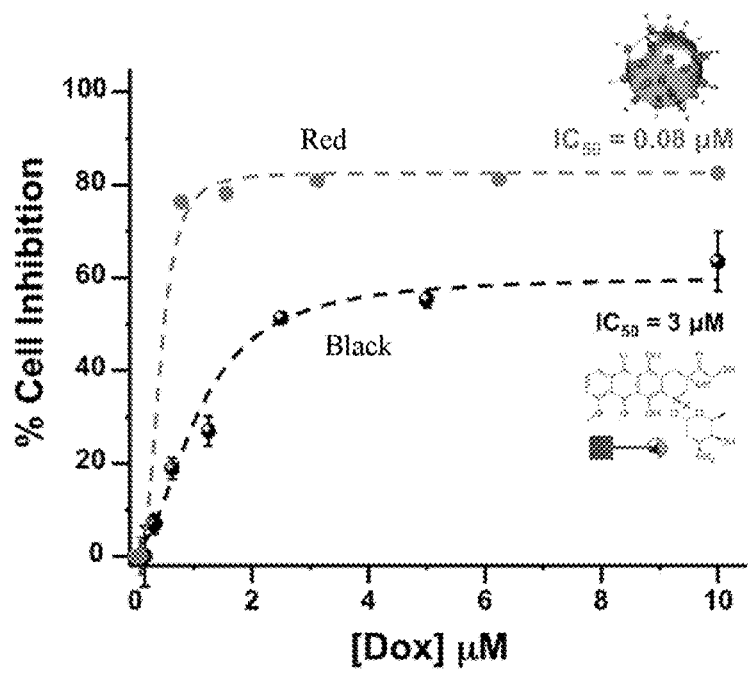
FIG. 29. Inhibition of HeLa cell proliferation after 48 hours plotted against concentration of free Dox (dashed black curve) and Dox-CB[7]NPs (dashed red curve)
Figure 30:
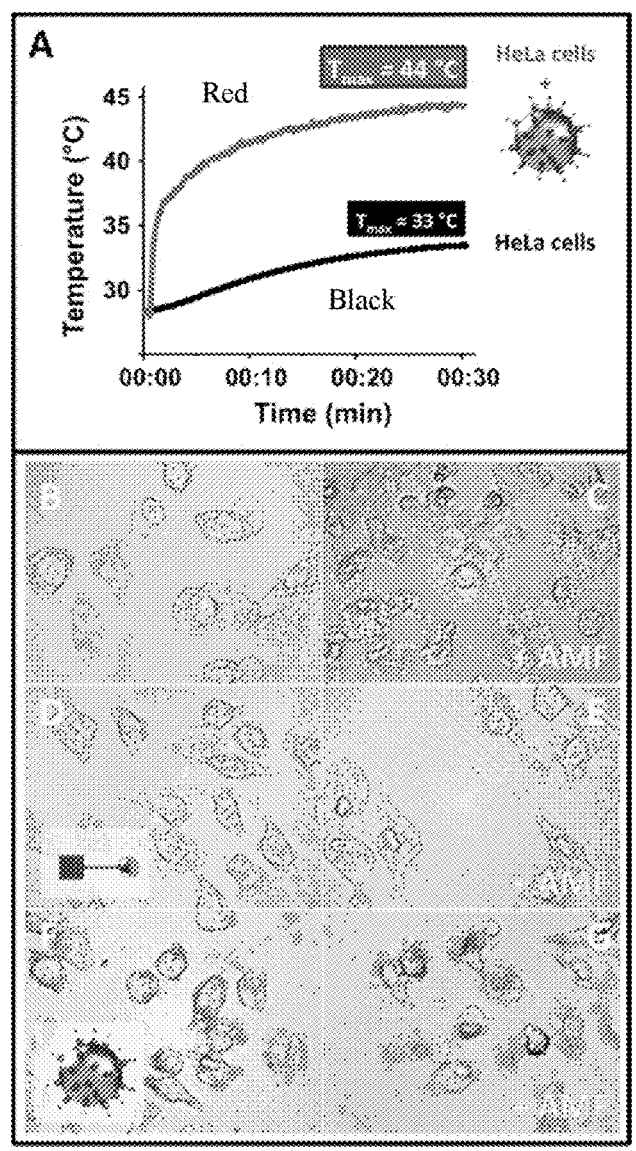
FIG. 30. Top: A) Temperature of HeLa cells (black curve) and HeLa cells in the presence of Dox-CB[7]NPs (red curve) over thirty minutes of magnetic field application (464 kHz) prior to magnetic treatment cells were incubated with Dox-CB[7]NPs for 2 hours). Bottom: Optical images of HeLa cells before (B, D, F) and after (C, E, G) magnetically induced hyperthermia treatment. Cells were exposed to the following conditions for two hours: no treatment (A, B), Dox (C, D), or Dox-CB[7]NPs (E, F).

The enhancement of the cell uptake of Dox using CB[7] NPs was clearly reflected on the cell viability tests that were performed on HeLa cells in order to evaluate the cytotoxicity of Dox-CB[7]NPs compared to Dox itself. After treating Hela cells with the same dose of Dox either using Dox-CB[7]NPs or Dox for 48 hours, inhibition of Hela cell growth was measured and the $IC_{50}$ values of Dox-CB[7]NPs and Dox were calculated to be 80 nM and 3 µM respectively (FIG. 30 29). These results demonstrate that Dox-CB[7]NPs have a significant higher cytotoxicity (as $1/40^{th}$ of the dose of free Dox is required to achieve the same level of cell inhibition).

With the chemotherapeutic character of the drug-loaded nanocarrier demonstrated in vitro, HeLa cells incubated with Dox-CB[7]NPs were subjected to AMF in order to evaluate the hyperthermia ability of the CB[7]NPs in vitro. Hela cells with no additives, or incubated with Dox or CB[7]NPs were also tested as control experiments. The temperature increase of the cells during the magnetic hyperthermia treatment was recorded using an external probe placed in the medium of cells subjected to hyperthermia treatment. The temperature of cells that had been incubated with Dox-CB[7]NPs rose to 44° C., whereas the temperature of untreated cells increased to only 33° C. (FIG. 30A). Confocal laser scanning microscopy revealed the morphology of the cells after hyperthermia sessions of one-hour duration. We noticed morphological changes only in Dox-CB[7]NP treated HeLa cells (FIG. 30E, F), with most of the cells being apoptotic (FIG. 30B) and displayed loss of membrane integrity. Untreated cells (FIG. 30A, B) and those treated with free Dox alone (FIG. 30C, D) had normal morphology after one hour.

Figure 31:
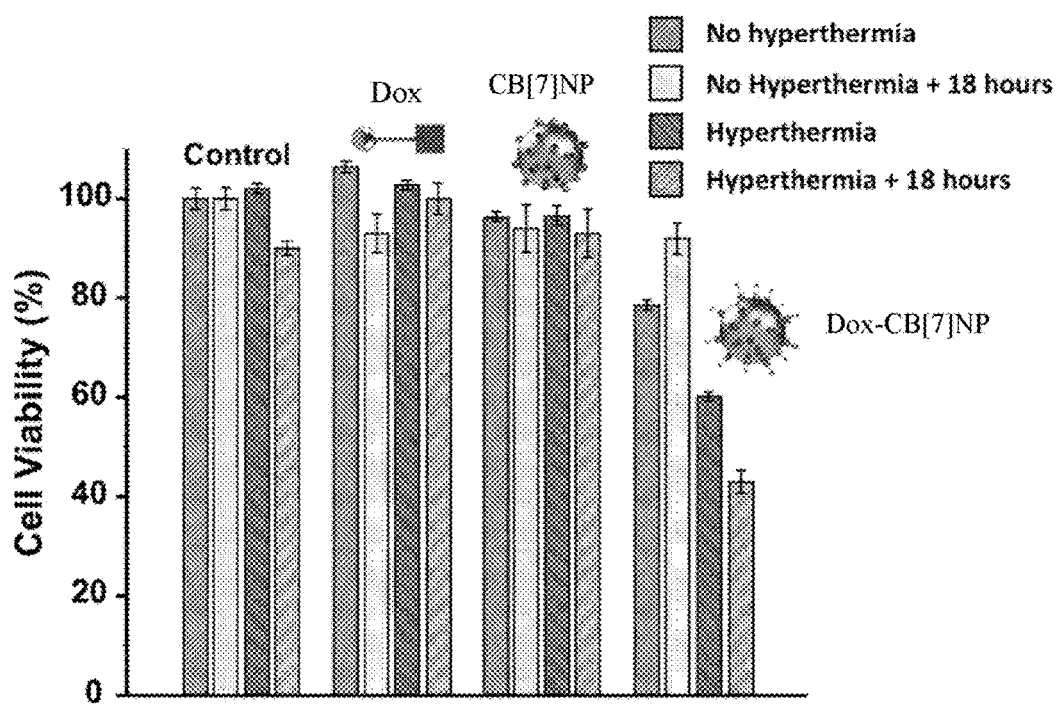
FIG. 31. Measurement of HeLa cell viability after incubation for two hours with cell-medium alone (control), Dox (red bar), CB[7]NPs (sphere with yellow studs) or Dox-CB [7]NPs (sphere with yellow and pink studs). One sample in each treatment group was subjected to an oscillating magnetic field (464 kHz) to induce hyperthermia. Cell viability was measured immediately after the final treatment and 18 hours after the final treatment. For each set, the bars represent from left to right: No hyperthermia; No hyperthermia+ 18 hours; Hyperthermia; and Hyperthermia+18 hours.

Cell viability tests in presence and in absence of AMF were performed in order to evaluate the effect of combined treatments (hyperthermia and chemotherapy) on HeLa cell viability (FIG. 31). Hela cells were incubated for two hours with no additives, Dox, CB[7]NPs or Dox-CB[7]NPs. Selected samples were then subjected to an alternating magnetic field (464 kHz) for one hour. Minimal reductions in viability were observed in the samples that had been incubated with no additives, Dox, or CB[7]NPs with or without hyperthermia treatments. The lack of significant cytotoxicity in the cells incubated with Dox or CB[7]NPs is consistent with the limited cellular uptake of the free drug or the lack of toxicity of the nanocarrier respectively. The viability of cells incubated with Dox-CB[7]NPs was initially reduced 70%, and these cells recovered to about 90% viability after 18 hours. In contrast, the combination of Dox-CB[7]NP-incubation and hyperthermia treatment reduced viability to 60% initially and then to 43% after 18 hours, demonstrating a pronounced combined effect.

General Methods. All reagents were purchased from commercial supplier (Sigma-Aldrich) and used without further purification. Nanopure water (conductivity of 0.06 µS cm$^{-1}$), obtained from a Millipore Gradiant Elix-3/A10 system was used to prepare the sample solutions. Iron concentration was deduced from UV-Visible absorption spectra recorded with an Agilent Technologies Cary 5000 Series UV-Vis-NIR Spectrophotometer in water at room temperature (298 K). Solutions were examined in 1 cm spectrofluorimetric quartz cells. The experimental error of the wavelength values was estimated to be ±1 nm. Infrared spectra were recorded on an Agilent Technologies Cary 600 Series FTIR Spectrometer using the ATR mode. Thermogravimetric Analyses were performed on a TA SDT Q600 device. Proton Nuclear magnetic resonance ($^1$H NMR) spectra were recorded at 298 K on a Bruker Advance 500 spectrometer with a working frequency of 500 MHz. Chemical shifts are reported in ppm relative to the signals corresponding to the residual non-deuterated solvent ($D_2O$ ($\delta$=4.97)). Magnetic properties of the nanoparticles were studied using a vibrating sample magnetometer, VSM (Quantum Design, Versalab). Emission spectra in water at room temperature were recorded on a Perkin Elmer LS55 Fluorescence Spectrometer using an excitation wavelength of 488 nm, which corresponds to the maximum absorption of Doxorubicin. Phase contrast and fluorescence images were observed on a LEICA DMI 2000B confocal scanning microscope. The nanoparticles were heated using magneTherm, a device that allows magnetic fluid and nanoparticle hyperthermia testing.

Synthesis. Surface functionalization of NPs with CB[7]. Iron oxide nanoparticles surface functionalized with cucrbit [7]uril (CB[7]) were synthesized as described above.

Encapsulation of Doxorubicine (Dox) by CB[7] on CB[7] NPs. CB[7]NPs ($n_{CB[7]}$=1.3×10$^{-4}$ mol) and Dox (1.5×10$^{-4}$ mol) were mixed in water (V=3 ml, CB[7]/Dox, 1:1.1) and stirred for twenty-four hours at room temperature and pH 7 to form inclusion complexes on the surface of NPs. Slow dialysis was used to remove excess doxorubicin that was not encapsulated in CB[7]NPs. The brown precipitate, Dox-CB[7]NPs, that resulted after dialysis was analysed by FTIR, TGA and ζ-potential measurements to confirm and quantify the encapsulation of Dox into CB[7]NPs.

NP Characterization. Fourier Transform Infrared (FTIR) Spectroscopy. The encapsulation of Dox within CB[7] on CB[7]NPs was confirmed and characterized using an Agilent Technologies Cary 600 Series FTIR Spectrometer.

Figure 32:
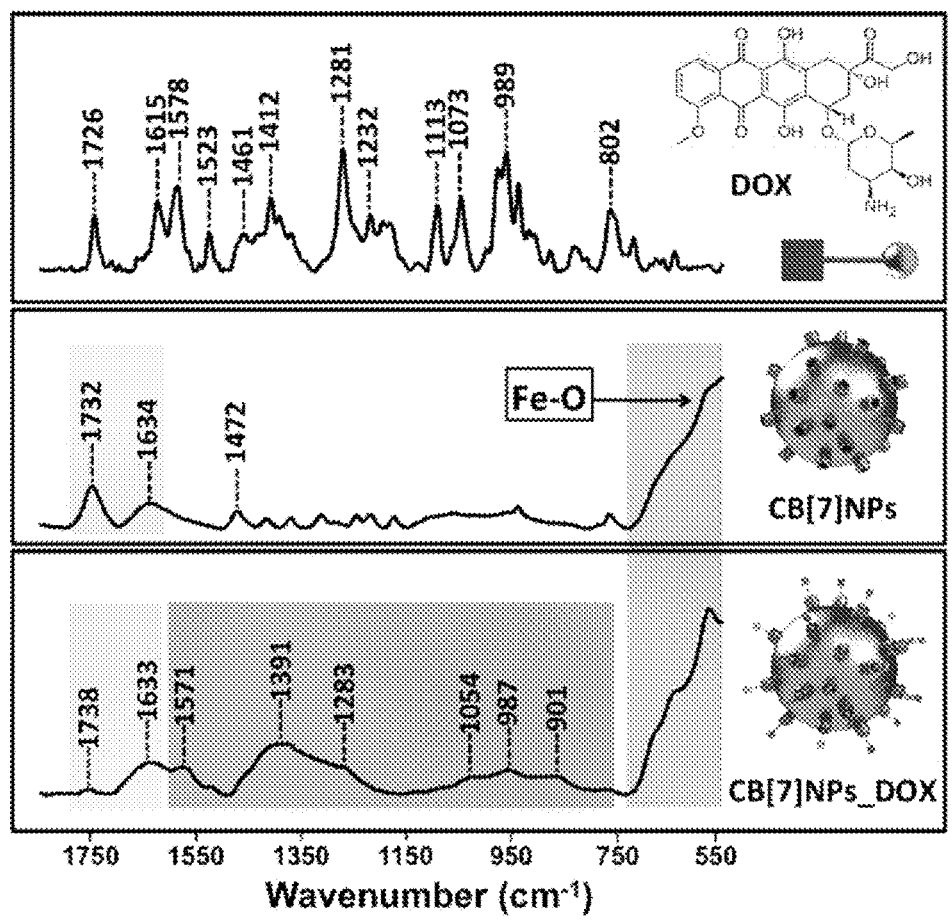
FIG. 32. FTIR spectra of (A) free Dox, (B) CB[7]NPs and (C) Dox-CB[7]NPs.

The presence of iron oxide band at ~600 cm$^{-1}$ of Dox-CB[7]NPs shows that the CB[7]NPs is preserved. The presence of Dox within the CB[7]NPs complex is confirmed by the appearance of new peaks between ~1600 and 900 cm$^{-1}$ as seen in FIG. 32. The shifting of the original CB[7]NPs peaks and the appearance of new peaks confirms the encapsulation of Dox into CB[7]. The spectrum of Dox-CB[7]NPs is not simply the sum of the various separate components, hence confirming the encapsulation of Dox into CB[7]NPs.

Figure 33:
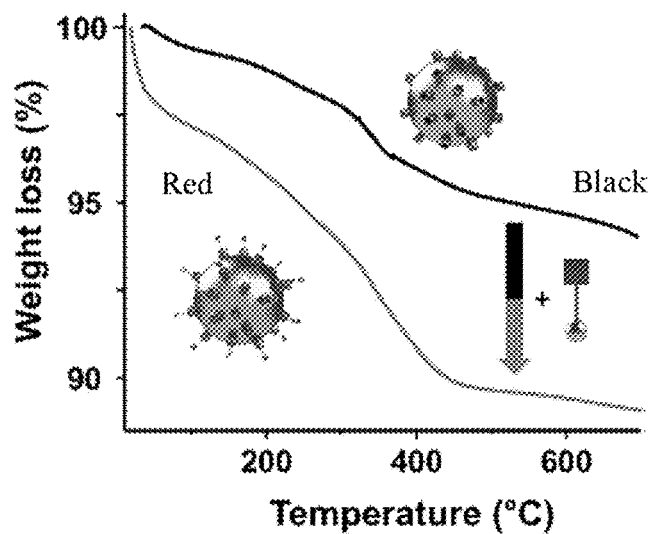
FIG. 33. Thermo-gravimetric analysis of CB[7]NPs (black) and Dox-CB[7]NPs (red).

Thermogravimetric Analysis (TGA). The weight percentage of Dox encapsulated by CB[7] on CB[7]NPs on the surface of CB[7]NPs was determined by TGA. Solid samples (10 mg) under $N_2(g)$ flux were characterized with a SDT Q600 TA Instruments analyzer at a heating rate of 5° C./min over a temperature range of 35-700° C. FIG. 33 presents the weight losses of CB[7]NPs before (black curve) and after (red curve) encapsulation of the Dox. An additional weight loss that corresponds to Dox is observed. These data clearly testify to the successful encapsulation of DPV$^{2+}$ into the cavities of the CB[7] macrocycles. The TGA analysis of Dox-CB[7]NPs shows a composition of 88.2% iron oxide, 5.06% of water, 4.14% of CB[7] and 2.06% of Dox corresponding to a 1:1 guest-host complexation (Dox/CB[7]) (Table 4). Dox molecules interacted with 28 macrocycles on the surface of the NPs at a 1:1 host/guest ratio (FIG. 33).

TABLE 4

TGA calculations for Dox-CB[7]NPs.

|  | Weight loss (%) | Mass in 1 g (g) | n in 1 g (mol) |
|---|---|---|---|
| γ-Fe$_2$O$_3$ (NPs) | 88.2 | 0.88 | $n_{NP}$ = 2.5 × 10$^{-7}$ |
| CB[7] | 4.14 | 0.04 | 4.0 × 10$^{-5}$ |
| Dox | 2.06 | 0.02 | 4.0 × 10$^{-5}$ |

Dynamic Light Scattering (DLS) Characterization. DLS measurements were carried out on a Zetasizer Nano-ZS (Malvern Instruments) to determine the ζ-potential. All samples were analyzed at room temperature in water with diluted ferrofluid ([Fe]=1×10$^{-3}$ M).

Figure 34:
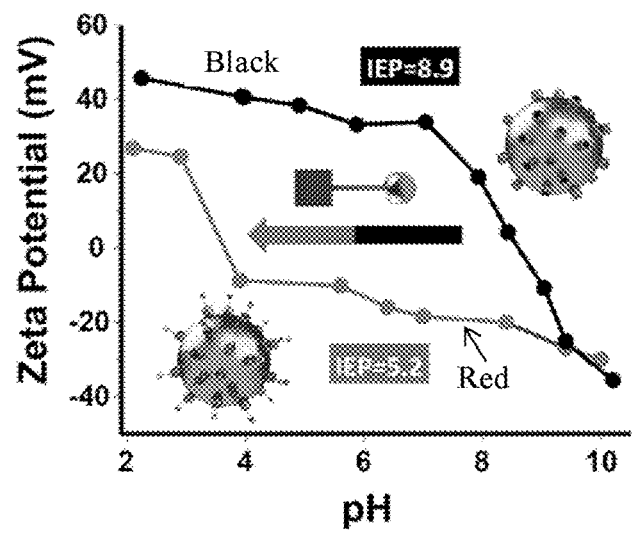
FIG. 34. Zeta potential results of Dox-CB[7]NPs (red) and CB[7]NPs (black) as function of pH.

At pH 7, ζ-potential of CB[7]NPs moves from +35 mV to −20 mV when Dox is encapsulated in CB[7]NPs (FIG. 34). This change in surface charge causes enough repulsion between Dox-CB[7]NPs to stabilize it. The isoelectric point also shifts from pH of 8.9 to pH of 5 upon Dox encapsulation. This surface modification is evidence of successful loading of Dox into CB[7]NPs.

Magnetic property studies Magnetic properties of the CB[7]NPs and Dox-CB[7]NPs, were studied using a vibrating sample magnetometer, VSM (Quantum Design, Versalab).

Figure 35:
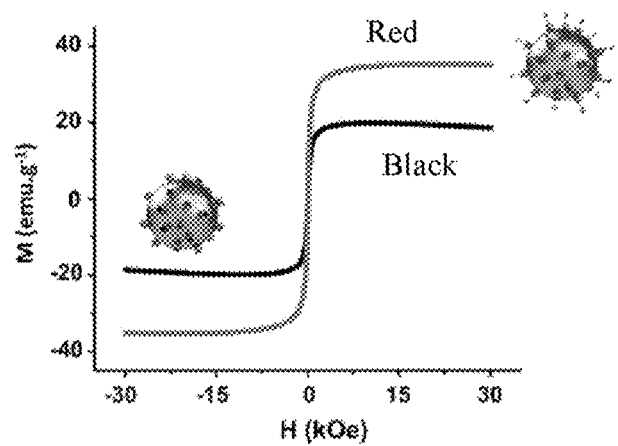
FIG. 35. Field dependence of the magnetization at 300 K of CB[7]NPs (black curve) and Dox-CB[7]NPs (red curve).

The VSM measures the magnetization by cycling the applied field from −30000 to 30000 Oe with a step rate of 100 Oe·s-1 for two times. Measurements were performed on powder samples at to 310 K. Field dependence of the magnetization is shown in FIG. 35.

Heating properties of Dox-CB[7]NPs using alternating magnetic field (AMF). The effect of AMF on the temperature of Dox-CB[7]NPs solution compared to NPCB[7]s and uncoated NPs was investigated using a magneTherm. The device produced alternating current (AC) magnetic field of frequency 464 kHz and a current of 26.8 kAm$^{-1}$. Samples ([Iron]=0.2M) of NPs, Dox-CB[7]NPs and CB[7]NPs was placed inside the magneTherm for 2 hours. The temperature of the samples with respect to time was measured and recorded using an external probe placed in the solution.

Release studies. pH dependent release of Dox from CB[7]NPs. The effect of pH on release of Dox from NPCB [7] was investigated at pH 7.4 and 5.5 over time. pH of the solutions were adjusted using NaOH and HCl solutions (1M). At each time, solutions were centrifuged and supernatants were collected and intensity of fluorescence was measured in comparison to a calibration curve.

Glutathione dependent release of DOX from CB[7]NPs. The effect of competitive guest dependant release of Dox from CB[7]NPs was investigated at pH 7.4 and in presence of Glutathione (10 mM) over time. pH of the solutions were adjusted using NaOH and HCl solutions (1M). At each time, solutions were centrifuged and supernatants were collected and intensity of fluorescence was measured in comparison to a calibration curve.

Temperature dependent release of Dox from CB[7]NPs. Prior to in vitro study, release of Dox from CB[7]NPs due to temperature change was studied. The effect of temperature on release of Dox from CB[7]NPs was investigated by heating Dox-CB[7]NPs solution ([Dox]=130 μM, [Iron]=0.1M) to 37° C., 39° C., 43° C. and 46° C. using Thermomixer comfort (eppendorf, 1.5 mL). After heating to specific temperature, solutions were centrifuged to remove CB[7]NPs. Supernatants were collected and intensity of fluorescence was measured and compared to fluorescence of supernatant collected at 25° C. to check for the effect of temperature of Dox release.

Biological studies. Cell studies and culture. A cervical cancer cell line (HeLa) was obtained from the American Tissue-Type Culture Collections (ATCC). Cells were cultured in Dulbecco's Modified Eagle's medium (DMEM), 10% fetal bovine serum (FBS), 1% penicillin/streptomycin and 20 mL L-Glutamine at 5% $CO_2$ and 37° C.

In vitro cellular uptake. The intracellular uptake of Dox-CB[7]NPs was studied using confocal microscopy. Petri-dishes with HeLa cells (~50000 cells/mL) were prepared and incubated. After 24 hours, DMEM was removed and cells were incubated for 2 hours with the following conditions: DMEM (control), Dox ([Dox]=76 μM) and Dox-CB[7]NPs ([Dox]=76 μM, [Iron]=0.04 M). After 2 hours of incubation, DMEM solution in the petri-dishes was removed and the cells were washed three times with phosphate buffered saline (PBS, Amresco Biotechnolgy grade). One petri-dish from each condition was subjected to one hour of magnetic hyperthermia (frequency 464 kHz, current 26.8 kAm$^{-1}$) while other petri-dishes were used as control to observe the effect of hyperthermia on the cellular internalization of Dox.

After magnetic hyperthermia treatment, DMEM was removed, the cells were washed with PBS three times and 1 ml of prepared formaldehyde solution ($V_{formaldehyde}$ 1 mL, $V_{distilled\ water}$ 9 mL) was added to the cells for 1 second to fix them. After removal of formaldehyde solution the cells were allowed to dry at room temperature for 48 hours in a dark place to prevent photodegradation of Dox. Confocal microscopy was used to confirm the internalization of Dox in the treated cells compared with control cells.

Internalization pathway studies. For these experiments, cells were incubated with endocytic inhibitors 30 min prior to nanoparticle addition. These were incubated for 2 hours and then washed with fresh medium before imaging. Table 5 summarizes the concentrations used for the endocytic inhibitors:

TABLE 5

Concentration of endocytic inhibitors used in this study.

| Endocytic Inhibitor | Concentration (μM) |
| --- | --- |
| Cloroquine (CQN) | 75 |
| Methyl-B-Cyclodextrin (MBCD) | 10 |
| Filipin (FLP) | 4.6 |
| Cytochalasin (CLN) | 20 |
| Chlorpromazine (CPZ) | 10 |

Figure 36:
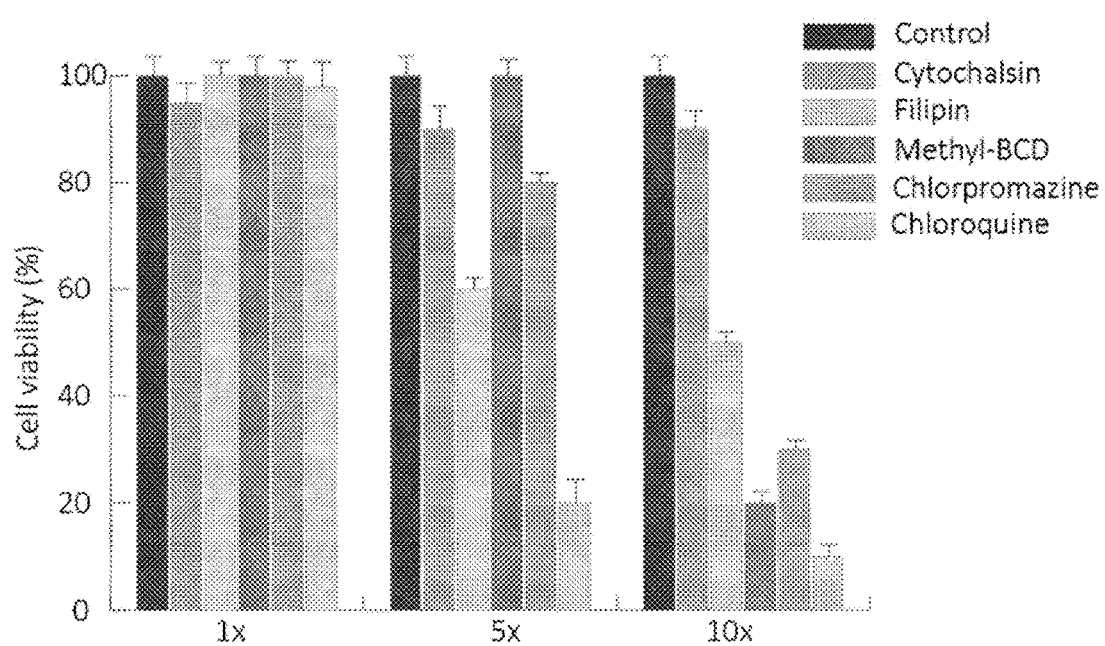
FIG. 36. Representations of cell viability tests. For each set, the bars represent from left to right: Control, Cytochalsin, Filipin, Methyl-BCD, Chlorpromazine, and Chloroquine.

Cell viability tests were also performed to minimize any experimental artefact that might be due to the cellular condition after drug addition. FIG. 36 shows that cell death was negligible for the concentrations used and increased only at 10 fold concentrations.

In vitro cell viability assay. The effect of Dox and Dox-CB[7]NPs was studied using the CellTiter-Blue® Cell Viability assay (CTB, Promega) which measures the metabolic activity of the cells. The reduction of the reagent dye resazurin into fluorescent resorufin due provides a measure of cell viability. Resorufin diffuses out of the cell into the medium after its formation. The fluorescent intensity of medium will indicate the toxicity of the drug as only viable cells have the ability to breakdown resazurin and its breakdown is proportional to the number of viable cells present. To determine the anti-cancer properties and efficacy of Dox-CB[7]NPs in Dox delivery, inhibition of HeLA cell growth with Dox-CB[7]NPs and with free Dox was studied.

Two 96 well plate of HeLa cells (~5000 cells/100 μL) were prepared and incubated at 37° C. After 24 hours, DMEM from one of the well plates was removed and replaced with various concentrations of Dox solution ([Dox]=5 μM, 10 μM, 15 μM, 20 μM, 30 μM, and 50 μM, respectively). The DMEM in the second well plate was replaced with different concentrations of Dox-CB[7]NPs ([Dox]=5 μM, 10 μM, 15 μM, 20 μM, 30 μM, and 50 μM, respectively). The well plates were incubated at 37° C. for 48 hours, after which cells were washed with PBS and incubated with 20 μL CTB per 100 μL of DMEM for an additional 6 hours at 37° C. The fluorescence emission of the medium at 590 nm was measured. The blank control was performed using just medium and CTB. The fluorescent intensity of CTB was used to determine and compare the concentration of Dox that decreased 50% of cell growth [inhibitory concentration 50% ($IC_{50}$)].

The percentage of cell inhibition and cell viability was calculated using the following formula:

Viability (%)=[($F_{treated}-F_{blank}$)/($F_{control}-F_{blank}$)]×100

Inhibition (%)=100−viability (%)

In vitro heating properties of Dox-CB[7]NPs. In vitro heating property of Dox-CB[7]NPs was studied by incubating HeLa cells with Dox-CB[7]NPs and subjecting them to magnetic hyperthermia using AMF. Two petri-dishes with HeLa cells (~50000 cell/mL) were seeded. After 24 hours, DMEM from one of the petri-dishes was removed, replaced with 1 mL of Dox-CB[7]NPs solution ([Iron]=0.04M, [Dox]=76 μM) mixed with DMEM and incubated for 2 hours. At the end of the treatment, the solution of Dox-CB[7]NPs was removed and the cells were very gently washed with PBS 3-4 times. 1 mL of DMEM was added to the petri-dishes and the cells were treated with magnetic hyperthermia for 30 minutes. Similar PBS wash procedure was followed with untreated HeLa cells before subjecting them to magnetic hyperthermia treatment. The temperature increase of the cells during the magnetic hyperthermia treatment was recorded using an external probe placed in the medium of cells subjected to hyperthermia treatment.

In vitro hyperthermia treatment. Viability tests on HeLa cells were performed to investigate the combined effect of both hyperthermia and chemotherapy treatment. Petri-dishes were seeded with HeLa cells (~50000 cells/mL) and incubated at 37° C. After 24 hours, DMEM was removed, replaced with the following solutions: DMEM (control), Dox ([Dox]=76 μM) and Dox-CB[7]NPs ([Dox]=76 μM, [Iron]=0.04 M) and incubated for 2 hours. After the treatment, the cells were washed with PBS 3 times and 1 mL of DMEM was added. Two petri-dishes from each condition were subjected to one hour of magnetic hyperthermia (frequency=464 kHz, current=26.8 $kAm^{-1}$) while other petri-dishes were used as control to observe the effect of hyperthermia on viability of the cells. Two cell viability readings were taken, immediately after hyperthermia treatment and 18 hours after hyperthermia. For cell viability studies 200 μL of CTB per 1 mL of DMEM was added to each petri-dish and incubated for 6 hours after which the medium with CTB was transferred to 96 well plate to take the fluorescence reading.

Morphology of the cells after hyperthermia and chemotherapy. To assess changes in cell morphology, HeLa cells (~50000 cells/mL) were cultured in petri-dishes and incubated at 37° C. After 24 hours, DMEM was removed, replaced with the following solutions: DMEM (control), Dox ([Dox]=76 μM) and Dox-CB[7]NPs ([Dox]=76 μM, [Iron]=0.04 M) and incubated for 2 hours. After the treatment, the cells were washed with PBS 3 times and 1 mL of DMEM was added. One petri-dish from each condition was subjected to one hour of magnetic hyperthermia (frequency=464 kHz, current=26.8 $kAm^{-1}$) while other petri-dishes were used as control.

After magnetic hyperthermia treatment, DMEM was removed, the cells were washed with PBS three times and 1 ml of prepared formaldehyde solution ($V_{formaldehyde}$=1 mL, $V_{distilled\ water}$=9 mL) was added to the cells for 1 second to fix them. After removal of formaldehyde solution the cells were allowed to dry at room temperature for 48 hours in a dark place to prevent photodegradation of Dox. Confocal microscopy used observe changes in the morphology of treated cells compared to control cells.

Example 3

In this example, the cavities of the adsorbed CB[7] were used to load a anti-cancer drug used in Chemotherapy—Paclitaxel (PTX)—thus forming the NP-CB[7]-Drug complex. CB[7] is hydrophilic on the outside—thus allowing it to dissolve in hydrophilic solutions such as blood and water—and hydrophobic on the inside—thus allowing hydrophobic drugs such as PTX to bind to it. Thus, the drug's solubility in water increases.

Due to the size of the nanoparticles and the magnetic nature of the Iron Oxide NPs themselves, the NP-CB[7]-drug complex is also magnetic. This is one of features distinguishing this delivery system from the others. Other systems allow increased solubility and passive targeting, while in the present system, a magnetic field can be used to direct the loaded drug to the malignant tumor and keep the potent chemical from spreading elsewhere thus maximizing its efficiency, minimizing side effects, and reducing risk of killing healthy cells.

Once encapsulated, the surface modification of the drug loaded NPs were studied by Infra-red (IR) spectroscopy and by measuring the surface charge zeta-potential using dynamic light scattering (DLS). Techniques such as Ultra-violet Visible (UV-Vis) spectroscopy and thermo-gravimetric analysis can be used to quantify the amount of different molecules on the surface.

We measured the effectiveness of this system at delivering paclitaxel to the malignant cells in vitro in comparison to the usage of the drug on its own.

Encapsulation of the drug within the CB[7]. A quantity of the drug equivalent to the drug: NP-CB[7] ratio of 27:1 (i.e., 27 molecules of the drug per CB[7]NP) is used. Since each iron oxide particle has 27 CB[7] molecules functionalized on the surface, thus the drug: CB[7] molecules ratio is 1:1. The amount of the drug needed is added to the CB[7]NP solution. The pH of the solution is at 2 (for stability of the nanoparticles). The solution is then allowed to stir for 24 hours. Afterwards, a magnet is again used to wash the nanoparticles in order to remove the excess of the drug that was not encapsulated.

Fourier Transform Infrared Spectroscopy. In order to verify that the CB[7] was successfully functionalized on the surface of the NPs used and that the drugs used were encapsulated into the CB[7] pocket, Fourier transform infrared spectroscopy (FTIR) was used. The IR spectrum of free paclitaxel (PTX) has characteristic absorption peaks at 1734, 1644, 1369, 1242, and 1072 $cm^{-1}$, which correspond to $\nu(C=O)$, $\nu(C-C)$, $\nu(CH_3)$, $\nu(C-N)$, and $\nu(C-O)$ respectively. The FTIR spectrum of CB[7]NP shows the characteristic Fe—O bond stretch of iron oxide nanoparticles at about 600 $cm^{-1}$. It also shows vibrational bands associated with CB[7] macrocycles such as peaks at 1732 $cm^{-1}$ (uncomplexed C=O group) and 1636 $cm^{-1}$ (particle bound C=O group). Bands corresponding to C—C, C—N, and C—H vibrations are also present. The FTIR spectrum of NP-CB[7]-PTX shows that the CB[7]NPs is preserved in the presence of the ligand, as evidenced by the iron oxide band at ~600 $cm^{-1}$ and the band at 1723 $cm^{-1}$ which corresponds to the un-complexed carbonyl group of CB[7]. The presence of PTX within the CB[7]NP complex is confirmed by the appearance of new peaks at 1258 and 1022 $cm^{-1}$, within the NP-CB[7]-PTX spectrum, that correspond to the C—N and the C—O stretch respectively. The shifting of the original CB[7]NP peaks and the appearance of new peaks indicates the occurrence of a change: encapsulation of the drug. Thus, the FTIR spectrum of the nanoparticle-drug complex is not simply the sum of its constituents. This indicates that there is an interaction between the PTX and CB[7]NP, namely the formation of 1:1 inclusion complexes where PTX is encapsulated inside the surface adsorbed CB[7] macrocycles.

Thermo-Gravimetric Analysis. In order to further confirm the presence and encapsulation of the drugs into the CB[7] pockets of the nanoparticles, thermo-gravimetric analysis (TGA) was conducted (up to 800° C.). TGA is also used to quantify the composition ratio of each element constituting the nanoparticle-drug complex. For NP-CB[7]-PTX, results show a composition of 13% CB[7], 10% PTX, and 77% Iron oxide. This corresponds to a 1:1:8 molecules CB[7]:PTX:NP ratio. The 1:1 CB[7]-PTX ratio supports the encapsulation theory proving that each molecule of PTX is interacting with 1 macrocycle (and is thus most likely being encapsulated).

Dynamic Light Scattering (DLS) was used to determine the stability of the nanoparticle-drug system at physiological pH in comparison to the system without the drug. The $\zeta$-potential of the nanoparticle-drug complex is also measured across a pH range of 2 to 10. The $\zeta$-potential of untreated CB[7]-NPs at pH=2 is +38.9 mV. When the drug is added, the $\zeta$-potential decreases (at each respective pH). It has been shown that functionalizing the NPs with CB[7] leads to a system with a higher $\zeta$-potential in comparison to the nanoparticles alone. However, when compared to the NP-CB[7] system, the NP-CB[7]-drug system's $\zeta$-potential is much lower. The curve shifts to the left when the drug is encapsulated. This is due to the hydrophobicity and size of the encapsulated PTX. The isoelectric point also shifts to a leftwards. Most importantly, however, is that at physiological pH, the charge of the NP-CB[7]-PTX system is −16 mv. This charge, although not high, is enough to induce electrostatic repulsion between the particles.

At a low acidic pH, the NP-CB[7]-drug complex is positively charged (and thus has a high potential). As the pH increases, the number of hydronium ions in the solution decreases while the number of hydroxide ions increases. Thus, the charge of the overall molecule decreases until it becomes zero (overall charge of the molecule is zero—a zwitterion). This point is known as the isoelectric point (PI) of the NP-CB[7]-drug complex. At the isoelectric point, the nanoparticles are not charged and thus aggregate. The closer the PI is to 7.4, the less stable the NP-CB[7]-drug. As the pH continues to increase (past the pH=PI mark of each NP complex), the $\zeta$-potential of the NP-CB[7]-PTX complex becomes negative and continues to decrease. The negatively charged particles repel each other and thus are stable at their respective pHs.

In order to determine the effectiveness of our nanoparticle system, we conducted a cancer cell viability study on our nanoparticle-drug system and compared it to effectiveness of the free drug (without the NP system). The Promega CellTiter-Blue® Cell Viability Assay was used. The drug, in one condition, and the Drug-NP complex, in another, were incubated with HCT-116 colon cancer cells for 48 hours. Different concentrations of the drug were used (ranging from 0 nM to 500 nM). After the designated incubation time, the $IC_{50}$—the concentration of the drug needed to inhibit 50% of the cancer cells incubated—was then measured for both conditions. The results show that 71 nM of the free drug was needed in order to achieve 50% inhibition. However, when the drug was encapsulated into the nanoparticle system, only 8 nM of the drug was needed to achieve the same 50% inhibition. Thus, the quantity of the drug needed is significantly reduced.

The hydrophobic interactions that bind the drug tightly to the inside of the CB[7] pocket on the surface of the nanoparticles can be weakened thereby leading to the release of the drug. Due to CB[7]'s high affinity to positively charged ions, ions (such as $Na^+$) can compete with drug molecules and replace them inside the pocket, thus inducing drug release. Similarly, modification of pH—where the concentration of hydrogen ions varies—can also lead to the disengaging of the drug from the pockets. For example, in an acidic environment, the concentration of hydrogen ions is high. So, hydrogen ions compete with the drug for encapsulation within the macrocycles. This leads to the displacement of the drug.

While the present disclosure may be described through specific embodiments, routine modifications will be apparent to those skilled in the art and such modifications are intended to be within the scope of this disclosure.

What is claimed is:

1. An iron oxide nanoparticle having a diameter from 5 nm to 15 nm and having adsorbed on the surface thereof a plurality of cucurbituril[7] (CB[7]) molecules, wherein the CB[7] molecules are adsorbed on the iron oxide nanoparticle surface via carbonyl groups of the CB[7] molecules and wherein each CB[7] molecule encloses a hydrophobic cavity.

2. The iron oxide nanoparticle of claim 1, wherein one or more of the CB[7] molecules have at least a part of an active agent in the hydrophobic cavity.

3. The iron oxide nanoparticle of claim 2, wherein the active agent is a hydrophobic or hydrophilic molecule.

4. The iron oxide nanoparticle of claim 3, wherein the agent is a hydrophobic molecule selected from the group consisting of doxorubicin, cisplatin, paclitaxel, daunorubicin, alendronate, zoledronate and combinations thereof.

5. The iron oxide nanoparticle of claim 1, wherein the CB[7] molecules are adsorbed on at least 70%, 80%, 90%, 95%, 99% of the total surface area of the iron oxide nanoparticle.

6. The iron oxide nanoparticle of claim 2, wherein the active agent is a magnetic resonance imaging contrast agent.

7. A composition comprising a plurality of iron oxide nanoparticles of claim 1 in a carrier.

8. The composition of claim 7, wherein the carrier is a buffer at a physiological pH.

9. The composition of claim 7, where at least 70%, 80%, 90%, 95%, or 100% of the nanoparticles have a diameter of 8 nm to 10 nm.

10. The composition of claim 9, wherein one or more of the CB[7] molecules on the nanoparticles have one or more active agents in the cavity thereof.

11. A method of making iron oxide nanoparticles of claim 1 comprising:
    a) providing a plurality of iron oxide nanoparticles having a diameter of 5 nm to 15 nm in an aqueous medium;
    b) contacting the iron oxide nanoparticles with at least an excess of CB[7] molecules such that a plurality of CB[7] molecules are adsorbed on to the surface of the iron nanoparticles;
    c) separating the iron oxide nanoparticles having a plurality of CB[7] molecules chemisorbed on the surface thereof from free CB[7] molecules;
    d) contacting the iron oxide nanoparticle from c) with an active agent to form iron oxide nanoparticles having CB[7] molecules adsorbed on the surface, wherein one or more of the CB[7] molecules have one or more active agents in the cavity thereof.

12. The method of claim 11, wherein in step b), the number of molecules of CB[7] for each nanoparticle is at least 700.

13. The method of claim 12, wherein in step b), the number of molecules of CB[7] for each nanoparticle is about 1,000.

14. The method of claim 11, wherein the iron nanoparticles having a plurality of CB[7] molecules adsorbed on the surface thereof are separated from free CB[7] molecules by one or more washes with an aqueous solution.

15. The method of claim 11, wherein step d) also comprises heating the reaction mixture of iron oxide nanoparticles and CB[7] molecules by exposing to microwave radiation.

16. A method of delivering an active agent to an individual comprising:
 a) administering a composition of claim 7 to an individual;
 b) optionally, guiding the nanoparticles in the composition to a desired location;
 c) optionally, monitoring the transport of the nanoparticles;
 d) exposing the individual to an alternating electric field such that at least a portion of the active agent is released at the desired location from the CB[7] molecules chemisorbed on the surface of the iron oxide nanoparticles.

17. The method of claim 16, wherein the desired location comprises a tumor.

18. The method of claim 16, further comprising obtaining imaging data on the individual after administering the composition and before exposing the individual to an alternating electric field to determine the movement and location of the nanoparticles.

19. The method of claim 16, wherein the imaging data is obtained by magnetic resonance imaging.

* * * * *